(12) United States Patent
Fu et al.

(10) Patent No.: US 7,335,635 B2
(45) Date of Patent: Feb. 26, 2008

(54) 14-3-3 BINDING MOLECULES AS SENSITIZERS FOR ANTICANCER THERAPIES

(75) Inventors: Haian Fu, Atlanta, GA (US); Shane C. Masters, Augusta, GA (US)

(73) Assignee: Emory University, Atlanta, GA (US)

( * ) Notice: Subject to any disclaimer, the term of this patent is extended or adjusted under 35 U.S.C. 154(b) by 392 days.

(21) Appl. No.: 10/468,310

(22) PCT Filed: Feb. 20, 2002

(86) PCT No.: PCT/US02/04948

§ 371 (c)(1),
(2), (4) Date: Mar. 19, 2004

(87) PCT Pub. No.: WO02/067968

PCT Pub. Date: Sep. 6, 2002

(65) Prior Publication Data

US 2004/0152630 A1    Aug. 5, 2004

Related U.S. Application Data

(60) Provisional application No. 60/270,401, filed on Feb. 21, 2001.

(51) Int. Cl.
*A61K 38/00* (2006.01)
(52) U.S. Cl. ........................ 514/12; 530/324
(58) Field of Classification Search ..................... None
See application file for complete search history.

(56) References Cited

U.S. PATENT DOCUMENTS

| | | | |
|---|---|---|---|
| 5,597,719 A | 1/1997 | Freed et al. |
| 5,856,445 A | 1/1999 | Korsmeyer |
| 5,948,765 A | 9/1999 | Shaw et al. |
| 6,103,692 A | 8/2000 | Avruch et al. |

FOREIGN PATENT DOCUMENTS

| | | |
|---|---|---|
| WO | WO 97/33601 | 9/1997 |
| WO | WO 98/17682 | 4/1998 |

OTHER PUBLICATIONS

Skolnick et al. (Trends in Biotech., 18(1):34-39, 2000).*
Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Burgess et al, Journal of Cell Biology vol. 111 Nov. 1990 2129-2138.*
Lazar et al Molecular and Cellular Biology Mar. 1988 vol. 8 No. 3 1247-1252.*
Fu, H., et al., "14-3-3 Proteins: Structure, Function, and Regulation," *Annual Review of Pharmacology and Toxicology*, 2000, pp. 617-647, vol. 40.
Gurnani, M., et al., "Adenovirus-mediated p53 Gene Therapy has Greater Efficacy when Combined with Chemotherapy Against Human Head and Neck, Ovarian, Prostate, and Breast Cancer," *Cancer Chemotherapy and Pharmacology*, 1999, pp. 143-151, vol. 44(2).
Masters, S.C., et al., "14-3-3- Proteins Mediate an Essential Anti-Apoptotic Signal," *The Journal of Biological Chemistry*, 2001, pp. 45193-45200, vol. 276(48).
Nielsen, L.L., et al., "Adenovirus-mediated *p*53 Gene Therapy and Paclitaxel Have Synergistic Efficacy in Models of Human Head and Neck, Ovarian, Prostate, and Breast Cancer," *Clinical Cancer Research*, 1998, pp. 835-846, vol. 4.
Petosa, C., et al., "14-3-3ζ Binds a Phosphorylated Raf Peptide and an Unphosphorylated Peptide via its Conserved Amphipathic Groove", *Journal of Biological Chemistry*, 1998, pp. 16305-16310, vol. 273(26).
Wang, B., et al., "Isolation of High-Affinity Peptide Antagonists of 14-3-3 Proteins by Phage Display[†]," *Biochemistry*, 1999, pp. 12499-12504, vol. 38.
Dong, S., et al., "14-3-3 Integrates Pro-survival Signals Mediated by the AKT and MAPK Pathways in ZNF198-FGFR1 Transformed Hematopoietic Cells," *Blood*, Mar. 27, 2007, 38 pgs. (Epub ahead of print).
Aprelikova, O., and E.T. Liu, "Use of 14-3-3s as a Diagnostic Marker and Therapeutic Target," A Method to Diagnosis and Determine the Prognosis of Breast and/or Ovarian Cancers, Nov. 28, 2000.

(Continued)

*Primary Examiner*—Sheela J. Huff
(74) *Attorney, Agent, or Firm*—Alston & Bird LLP

(57) ABSTRACT

Methods are provided for enhancing the death of a neaplastic cell comprising the administration of a therapeutically effective concentration of a 14-3-3 antagonist and at least one antineoplastic therapeutic agent. The methods of the invention find use in improving the clinical outcome of a mammal having a neoplastic disorder and comprises administration to a mammal in need thereof at least one antineoplastic therapeutic agent in combination with a 14-3-3 antagonist. Further provided are pharmaceutical compositions having a therapeutically effective amount of a 14-3-3 antagonist and an antineoplastic therapeutic agent. Also provided are methods for identifying agents that selectively inhibit an interaction between a 14-3-3 polypeptide and a 14-3-3 ligand.

19 Claims, 11 Drawing Sheets

OTHER PUBLICATIONS

Bertram, P.G., et al., "The 14-3-3 Proteins Positively Regularte Rapamycin-Sensitive Signaling", *Current Biology*, 1998, pp. 1259-1267, vol. 8.

Brunet, A., et al., "Akt Promotes Cell Survival by Phosphorylating and Inhibiting a Forkhead Transcription Factor," *Cell*, 1999, pp. 857-868, vol. 96, Cell Press.

Campbell, J. K., et al., "Activation of the 43 kDa Inositol Polyphosphate 5-Phosphatase by 14-3-3$\zeta^{554}$," *Biochemistry*, 1997, pp. 15363-15370, vol. 36, American Chemical Society.

Chan, T.A., et al., "14-3σ is Required to Prevent Mitotic Catastrophe After DNA Damage," *Nature*, 1999, pp. 616-620, vol. 401, Macmillan Magazines Ltd.

Chan, T.A., et al., "Cooperative Effects of Genes Controlling the G2/M Checkpoint",*Genes & Dev.*, 2000, pp. 1584-1588, vol. 14.

Fu, H., et al., "Interaction of the Protein Kinase Raf-1 with 14-3-3 Proteins," *Science*, 1994, pp. 126-129, vol. 266.

Henricksson, et al., "14-3-3 Proteins are Required for the Inhibition of Ras by Exoenzyme S," *Biochem. J.*, 2000, pp. 697-701, vol. 349, Biochemical Society.

Hsu, S.Y., et al., "Interference of BAD (Bcl-xL/Bcl-2-Associated Death Promoter)- Induced Apoptosis in Mammalian Cells by 14-3-3 Isoforms and P11," *Molecular Endocrinol.*, 1997, pp. 1858-1867, vol. 11.

Korsmeyer, S.J., "BCL-2 Gene Family and the Regulation of Programmed Cell Death[1]," *Cancer Research*, 1999, pp. 16938-17005, (SUPPL)39.

Leffers, H., et al., "Molecular Cloning and Expression of the Transformation Sensitive Epithelial Marker Stratifin: A Member of a Protein Family that has been Involved in the Protein Kinase C Signalling Pathway," *J. Mol. Biol.*, 1993, pp. 982-998, vol. 231.

Liu, D., et al., "Crystal Structure of the Zeta Isoform of the 14-3-3 Protein," *Nature*, 1995, pp. 191-194, vol. 376.

Masters, S.C., et al., "Interaction of 14-3-3 with a Nonphosphorylated Protein Ligand, Exoenzyme S of *Pseudomonas aeruginosa*$^{554}$," *Biochemistry*, 1999, pp. 5216-5221, vol. 38, American Chemical Society.

Muslin, A.J., et al., "Interaction of 14-3-3 with Signaling Proteins is Mediated by the Recognition of Phosphoserine," *Cell*, 1996, pp. 889-897, vol. 84.

Nakanishi, K., et al., "Elevated Expression Levels of the 14-3-3 Family Proteins in Lung Cancer Tissue," *Human Antibodies*, 1997, pp. 189-194, vol. 8(4).

Ogihara, T. et al., 14-3-3 Protein Binds to Insulin Receptor Substrate-1, One of the Binding Sites of Which is in the Phosphotyrosine Binding Domain, *The Journal of Biological Chemisity*, 1997, pp. 25267-25274, vol. 272(40).

Porter, G.W., et al., "Dynamic 14-3-3/client Protein Interactions Integrate Survival and Apoptotic Pathways", *Seminars in Cancer Biology*, 2006, pp. 193-202, vol. 16.

Takihara, Y., et al., "Role of the β Isoform of 14-3-3 Proteins in Cellular Proliferation and Oncogenic Transformation," *Carcinogenesis*, 2000, pp. 2073-2077, vol. 21(11).

Wang, H., "Mutations in the Hydropohobic Surface of an Amphipathic Groove of 14-3-3ζ Disrupt Its Interaction with Raf-1 Kinase," *The Journal of Biological Chemistry*, 1998, pp. 16297-16304, vol. 273(26).

Xing, H., et al., "14-3-3 Proteins Block Apoptosis and Differentially Regulate MAPK Cascades", *The EMBO Journal*, 2000, pp. 349-358, vol. 19.

Yaffe, M.B., "The Structural Basis for 14-3-3: Phosphopeptide Binding Specificity," *Cell*, 1997, pp. 961-971, vol. 91.

Zha, J., et al., "Serine Phosphorylation of Death Agonist BAD in Response to Survival Factor Results in Binding to 14-3-3 Not BCL-$X_L$," *Cell*, 1996, pp. 619-628, vol. 87.

Zhang, L., et al., "Suppression of Apoptosis Signal-Regulating Kinase 1-induced Cell Death by 14-3-3 Proteins," *Proc. Natl. Acad. Sci.*, 1999, pp. 8511-8515, vol. 96, Cell Biology.

Zhang, L., et al., "Residues of 14-3-3ζRequired for Activation of Exoenzyme S of*Pseudomonas aeruginosa*$^{554}$," *Biochemistry*, 1999, pp. 12159-12164, vol. 38, American Chemical Society.

Zhang, L., et al., "Raf-1 Kinase and Exoenzyme S Interact with 14-3-3ζThrough a Common Site Involving Lysine49," *The Journal of Biological Chemistry*, 1997, pp. 13717-13724, vol. 272(21), The American Society for Biochemistry and Molecular Biology, Inc.

* cited by examiner

EYFP

EYFP-difopein 14-3-3 BINDING MOLECULES AS SENSITIZERS FOR ANTICANCER THERAPIES

CROSS-REFERENCE TO RELATED APPLICATIONS

This application is a U.S. National Phase of PCT Application No. PCT/US02/04948, filed Feb. 20, 2002, which claims the benefit of U.S. Provisional Application Ser. No. 60/270,401, filed Feb. 21, 2001, all of which are herein incorporated by reference.

FEDERALLY SPONSORED RESEARCH OR DEVELOPMENT

This research was funded in part by the National Institute of Health, contract number GM53165.

FIELD OF THE INVENTION

The present invention is directed to a method for enhancing the death of a neoplastic cell comprising the administration of a therapeutically effective concentration of a 14-3-3 antagonist and an antineoplastic therapeutic agent. The invention is further directed to methods of identifying 14-3-3 antagonists useful in the treatment of neoplastic disorders.

BACKGROUND OF THE INVENTION

Increased cell proliferation and loss of differentiation have long been recognized as two major factors that promote neoplastic transformation and progression. This understanding has contributed tremendously to the development of antineoplastic treatments aimed at suppressing cell proliferation. Antineoplastic therapies, including radiation and chemotherapeutic agents, ultimately eliminate tumor cells by the induction of apoptosis, a physiological process of cell destruction. Accumulating evidence suggests that expression of oncogenes sensitizes many primary tumors to apoptotic cell death as compared to their normal counterparts, which provides a critical therapeutic window for treatment. However, this therapeutic opportunity is eroded by antiapoptotic mechanisms that are conferred by mutations accumulated during the transformation process or induced upon treatment.

In metazoans oncogenic alterations often sensitize cells to apoptotic stimuli. For example, expression of oncogenic c-myc or the adenovirus early region 1A can increase cellular susceptibility to apoptosis in circumstances such as growth factor deprivation. This oncogenic-induced sensitization serves as a physiological barrier against tumor development by limiting the expansion of affected cells. Such sensitization to apoptosis by oncogenes also provides a therapeutic window for treating many tumors with anticancer agents. However, it is widely believed that host tumor surveillance mechanisms select for upregulation of antiapoptetic mechanisms during the process of transformation decreasing the therapeutic benefit of conventional anticancer drugs. Accordingly, by inhibiting critical antiapoptotic mechanisms, sensitivity of tumor cells to therapy-induced apoptosis may be restored.

14-3-3 proteins are dimeric, phosphoserine-binding molecules that interact with a number of phospho-proteins involved in controlling cell death and proliferation. 14-3-3 polypeptides supports cell survival by inhibiting the death promoting activity of its associated proapoptotic partners. One prominent target of the 14-3-3 polypeptide is Bad. Bad is a proapoptotic member of the Bcl-2 family of apoptosis regulators. Interestingly, Bad is phosphorylated by activated Akt and other kinases which generates a 14-3-3 recognition site, leading to Bad/14-3-3 complex formation. Thus, the phosphorylation of Bad couples multiple survival signaling pathways to the cell death machinery. Bad is not the only 14-3-3 target with death-promoting activity. ASK1, a Ser/Thr kinase, is a critical element of a death signaling pathway initiated by TNFα, Fas activation, and the chemotherapeutic agents paclitaxel and cisplatin. 14-3-3 binding suppresses the death-promoting activity of ASK1.

Inhibition of Bad-, ASK-, and FKHRL1-induced apoptosis by 14-3-3 raises the possibility that 14-3-3 functions as an antiapoptotic factor (Brunet et al. (1999) *Cell* 96:857-868; Zha et al. (1996) *Cell* 87:619-628; and Zhang et al. (1999) *Proc. Natl. Acad. Sci.* 96:8511-8515, all of which are herein incorporated by reference). Because 14-3-3 interacts with a large array of ligands involved in both cell death and cell survival, 14-3-3 may be part of a general antiapoptotic mechanism essential for cell survival. 14-3-3 could support cell survival both by suppressing the activity of proapoptotic proteins and by promoting the activity of antiapoptotic proteins.

Given the shortcomings of current chemotherapy and irradiation, namely the lack of response and resistance or tolerance to the various antineoplastic agents, there is a need for developing additional forms of treatment that can enhance a response of a neoplastic cell to the antineoplastic therapies. The present invention provides a novel method of treating a neoplastic disorder by modulating the activity of a 14-3-3 polypeptide.

SUMMARY OF THE INVENTION

Methods and compositions for enhancing the death of a neoplastic cell by modulating the activity of a 14-3-3 polypeptide are provided. More specifically, the present invention provides methods and compositions for enhancing the therapeutic effectiveness of an antineoplastic therapeutic agent.

In particular, the present invention provides a method for identifying an agent that selectively inhibits an interaction between a 14-3-3 polypeptide and a 14-3-3 ligand. The method comprises (a) contacting a 14-3-3 polypeptide with a 14-3-3 antagonist under conditions that permit formation of a 14-3-3/antagonist complex; (b) contacting the 14-3-3/antagonist complex with a candidate agent; and, (c) determining if the candidate agent disrupts the 14-3-3/antagonist complex. The 14-3-3 antagonist used in the methods of the invention comprises a polypeptide having an amino acid sequence of SEQ ID NO:1, 2, or a biologically active variants thereof.

In other embodiments of the present invention, the method of identifying an agent that selectively inhibits an interaction between a 14-3-3 polypeptide and a 14-3-3 ligand comprises (a) contacting a 14-3-3 polypeptide with a candidate agent under conditions that allow for a 14-3-3/candidate agent complex to form; (b) contacting said 14-3-3/candidate agent complex with a 14-3-3 antagonist; and (c) determining if the 14-3-3 antagonist disrupts the 14-3-3/candidate agent complex.

The present invention further comprises a pharmaceutical composition comprising a therapeutically effective amount of a 14-3-3 antagonist and at least one antineoplastic therapeutic agent. In one embodiment, the 14-3-3 antagonist comprises a polypeptide having an amino acid sequence of SEQ ID NO:1, 2, or a biologically active variant thereof. In other embodiments, the 14-3-3 antagonist comprises an agent identified by the methods of the present invention.

The invention further provides a method of enhancing the death of a neoplastic cell comprising providing to the neoplastic cell a therapeutically effective amount of a 14-3-3 antagonist and at least one antineoplastic therapeutic agent. The methods of the invention find further use in the treatment of neoplastic disorders by the administration of a therapeutically effective amount of a 14-3-3 antagonist and an antineoplastic therapeutic agent to a mammal in need thereof.

DETAILED DESCRIPTION OF THE INVENTION

Figure 1:
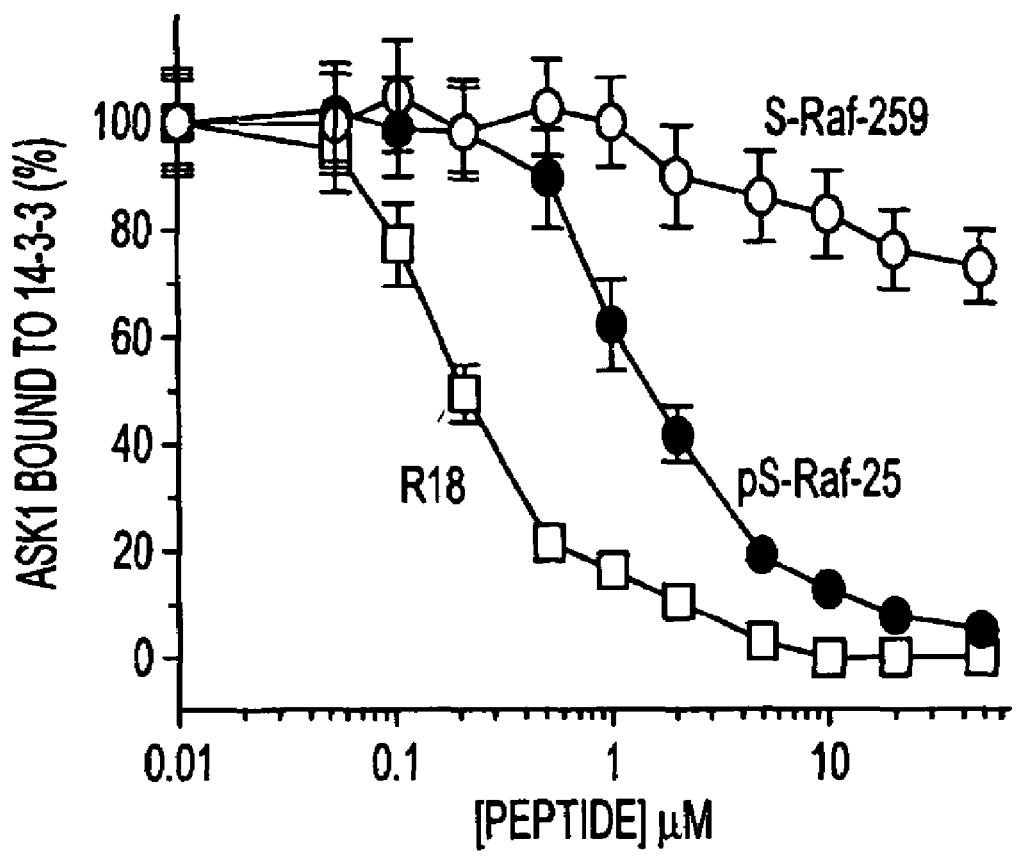
FIG. 1 demonstrates the inhibitory effect that the 14-3-3 antagonist R18 has on ASK1/14-3-3 interactions. The percentage of ASK1 bound to 14-3-3 relative to peptide-free samples is plotted against increasing concentrations of the test peptides.

The present invention is directed to the treatment of a neoplastic disorder. Specifically, the present invention provides a method for enhancing the death of a neoplastic cell comprising the administration of a therapeutically effective concentration of a 14-3-3 antagonist and at least one antineoplastic therapeutic agent. The methods find use in enhancing the death of a neoplastic cell as compared to administration of either agent alone. The methods of the present invention find use in overcoming the resistance of a cancer to a single therapeutic agent. The methods of the invention may further allow a lower effective dose of the antineoplastic therapeutic agent and thereby reduce the undesirable side effects associated therewith. Hence, the methods of the invention find use in improving the clinical outcome of a mammal having a neoplastic disorder comprising administration of an antineoplastic therapeutic agent in combination with a 14-3-3 antagonist.

By "14-3-3 polypeptide" is intended a member of the 14-3-3 protein family. 14-3-3 is a family of highly homologous proteins encoded by separate genes. There are seven known mammalian 14-3-3 isoforms, named with Greek letters ($\beta$, $\epsilon$, $\gamma$, $\eta$, $\sigma$, $\tau$, $\zeta$) after their elution profile on reversed phase high-performance liquid chromatography (Ichimura et al. (1988) *Proc. Natl. Acad. Sci.* USA 85:7084-7088 and Martin et al. (1993) *FEBS Lett.* 331:296-303). The species initially designated $\alpha$ and $\delta$ are actually the phosphorylated forms of $\beta$ and $\zeta$ (Aitken et al. (1995) *J. Biol. Chem.* 270:5706-5709). The 14-3-3 proteins exist mainly as dimers with a monomeric molecular mass of approximately 30,000 and an acidic isoelectric point of 4-5. General properties of the 14-3-3 polypeptides can further be found in Fu et al. (2000) *Annu. Rev. Pharmacol. Toxicol.* 40:617-647, herein incorporated by reference. The nucleic acid and amino acid sequences of various 14-3-3 family members can be found in, for example, Leffer et al. (1993) *J. Mol. Biol.* 231:982-998, which is herein incorporated by reference. Homologues of 14-3-3 proteins have also been found in a broad range of eukaryotic organisms. As discussed herein, the 14-3-3 polypeptides have a variety of biological functions. By "modulation of 14-3-3" activity is intended any alteration of the 14-3-3 polypeptide activity that results in disrupting the ability of the 14-3-3 polypeptide to interact with a 14-3-3 ligand, particularly a ligand comprising a proapoptotic polypeptide. Disruption of the 14-3-3 polypeptide/ligand interaction is characterized in vivo by enhanced cell death and/or the sensitization of the cell to antineoplastic therapeutic agents. In addition, the disruption of the 14-3-3 polypeptide/ligand interaction can further be characterized by alterations in cell differentiation, cell proliferation, cell cycle regulation, viral transformation, bacterial pathogenesis, or apoptosis. Both in vivo and in vitro assays that can be used to assay for these interactions are discussed more fully below.

As defined herein, a "14-3-3 antagonist" comprises a chemical compound, a mixture of chemical compounds, or a biological macromolecule that modulates the activity of the 14-3-3 polypeptide. The 14-3-3 antagonist of the invention can modulate the activity of the 14-3-3 polypeptide by interacting directly with the 14-3-3 polypeptide. In specific embodiments, the direct interaction of the 14-3-3 antagonist with the 14-3-3 polypeptide disrupts the interaction of the 14-3-3 polypeptide with a 14-3-3 ligand. For instance, the 14-3-3 antagonist can directly disrupt the interaction of the 14-3-3 polypeptide with a death-regulatory protein including, for example, Bad (Zha et al. (1996) *Cell* 87:619-628); ASK1 (Zhang et al. (1999) *Proc. Natl. Acad. Sci.* 96:8511-8515); p53; PI 3-kinase (Bonnefoy et al. (1995) *Proc. Natl. Acad. Sci.* 92:10142-10146); Bcr-Abl (Reuther et al. (1994) *Science* 266:129-133); IGF-IR (Craparo et al. (1997) *J. Biol. Chem.* 272:11663-11669); and Raf-1 (Fantl et al. (1994) *Nature* 371:612-614; Freed et al. (1994) *Science* 265:533-535; and Fu et al. (1994) *Science* 266:126-129). As discussed in more detail below, the 14-3-3 antagonist can comprise the amino acid sequence set forth in SEQ ID NO:1, 2 or biologically active variants thereof. In other embodiments the 14-3-3 antagonist comprises an agent identified by the methods described below.

The 14-3-3 polypeptide is dimeric and comprises two amphipathic peptide-binding grooves that are arranged in an antiparallel fashion (Liu et al. (1995) *Nature* 376:191-194 and Petosa et al. (1998) *J. Biol. Chem.* 273:16305-16310, both of which are herein incorporated by reference). The inner surface of the groove is formed by the four helices ($\alpha$3, $\alpha$5, $\alpha$7 and $\alpha$9) and is characterized as having a cluster of basic and polar residues (from $\alpha$3 and $\alpha$5) on one side and a cluster of hydrophobic residues (from $\alpha$7 and $\alpha$9) on the other side. The amphipathic groove may bind different peptide motifs and induce either homodimer or heterodimer formation in its target proteins (i.e., 14-3-3 ligands). Residues of the amphipathic groove of bovine 14-3-3 ζ include N38, E39, R41, N42, L43, S45, V46, K49, N50, V52, G53, R56, S57, R60, E113, F117, K120, M121, D124, Y125, R127, Y128, P165, I166, G169, L172, N173, V176, Y179, E180, D213, L216, I217, L220, D223, N224, L227, W228.

As used herein, a "14-3-3 amphipathic groove binding antagonist" interacts with the 14-3-3 polypeptide with at least one of the amino acids comprising the conserved amphipathic groove of the 14-3-3 polypeptide dimer and thereby prevents the association of 14-3-3 ligands that interact at the amphipathic groove. See, for example, Petosa et al. (1998) *The Journal of Biological Chemistry* 273: 16305-16310, herein incorporated by reference, for the crystal structure of the amphipathic groove. Petosa et al. further show that the 14-3-3 antagonist provided in SEQ ID NO:1 is a 14-3-3 amphipathic groove binding antagonist. The 14-3-3 antagonist set forth in SEQ ID NO:2 is also an amphipathic groove binding antagonist. As demonstrated elsewhere herein, the binding of the 14-3-3 antagonist of SEQ ID NO:2 (difopein) inhibits the interaction of the 14-3-3 polypeptide with Raf-1, a prototypical 14-3-3 amphipathic groove binding protein.

It is further recognized that the 14-3-3 antagonist used in the methods of the present invention may indirectly modulate the activity of the 14-3-3 polypeptide. An indirect interaction encompasses, for example, an alteration in the activity of a polypeptide that influences the ability of the 14-3-3 polypeptide to interact with a 14-3-3 ligand (i.e., a proapoptotic protein). For instance, the interaction of the 14-3-3 polypeptide with many of the ligands is regulated by specific phosphorylation of the 14-3-3 ligand. The activities of the kinases that phosphorylate these ligands can therefore regulate 14-3-3 polypeptide/ligand interactions. See, for example, Muslin et al. (1996) *Cell* 84:889-897; Yaffe et al. (1997) *Cell* 91:961-971; and Furakawa et al. (1993) *Biochem. Biophys. Res. Commun.* 194:144-149, all of which are herein incorporated by reference. Hence, in specific embodiments of the present invention, the 14-3-3 antagonist can act indirectly on the 14-3-3 polypeptide by influencing regulatory factors, such as kinases that regulate the phosphorylation state of the various 14-3-3 ligands.

Administration of the 14-3-3 antagonist to a cell enhances cell death. By "enhance" is intended any increase in the level of cell death upon administration of the 14-3-3 antagonist when compared to the extent of cell death occurring in the absence of the 14-3-3 antagonist. Administration of the 14-3-3 antagonist results in the enhanced susceptibility or sensitization of a neoplastic cell to respond to an antineoplastic therapeutic agent. By "sensitization" is intended the combined administration of the antineoplastic therapeutic agent and the 14-3-3 antagonist produces an anti-cancer effect (i.e., prohibition of cellular proliferation or potentiation of cell death) which exceeds the therapeutic effect of either the 14-3-3 antagonist and the antineoplastic therapeutic agent alone.

The present invention therefore provides a method to treat a neoplastic disease or disorder. By "treatment or prevention" is intended the alleviation of the signs, symptoms, or causes of a disease, or any other desired alteration of a biological system. Accordingly, the method of the invention "prevents" (i.e., delays or inhibits) and/or "reduces" (i.e., decrease, slows, or ameliorates) the detrimental effects of the neoplastic disease or disorder in the mammal receiving the therapy.

As used herein, a "neoplastic disease or disorder" is characterized by one or more of the following properties: cell growth is not regulated by the normal biochemical and physical influences in the environment; anaplasia (i.e., lack of normal coordinated cell differentiation); and in some instances, metastasis. The term cancer, neoplasia, and malignancy are used interchangeably herein. Neoplastic diseases include, for example, anal carcinoma, bladder carcinoma, breast carcinoma, cervix carcinoma, chronic lymphocytic leukemia, chronic myelogenous leukemia, endometrial carcinoma, hairy cell leukemia, head and neck carcinoma, lung (small cell) carcinoma, multiple myeloma, non-Hodgkin's lymphoma, follicular lymphoma, ovarian carcinoma, brain tumors, colorectal carcinoma, hepatocellular carcinoma, Kaposi's sarcoma, lung (non-small cell carcinoma), melanoma, pancreatic carcinoma, prostate carcinoma, renal cell carcinoma, and soft tissue sarcoma. Additional neoplastic disorders can be found in, for example, Isselbacher et al. (1994) *Harrison's Principles of Internal Medicine* 1814-1877, herein incorporated by reference.

Any antineoplastic agent (i.e., chemotherapeutic, radiation, or biological response modifiers) can be used in the methods of the present invention. It is understood that the antineoplastic agent may affect neoplastic cells by a variety of mechanisms, including killing or decreasing viability, by apoptosis or various other cellular mechanisms. Regardless of the mechanism of the antineoplastic agent, the 14-3-3 antagonist will sensitize the neoplastic cell to the antineoplastic agent. In any particular embodiment of the invention, the antineoplastic therapeutic agent will be selected with reference to factors such as the type of neoplastic disorder and the efficacy of the antineoplastic agent for treating the desired neoplastic disorder.

Chemotherapeutic agents include, but are not limited to, Aminoglutethimide; Asparaginase; Bleomycin; Busulfan; Carboplatin; Carmustine (BCNU); Chlorambucil; Cisplatin (cis-DDP); Cyclophosphamide; Cytarabine HCl; Dacarbazine; Dactinomycin; Daunorubicin HCl; Doxorubicin HCl; Estramustine phosphate sodium; Etoposide (VP-16); Floxuridine; Fluorouracil (5-FU); Flutamide; Hydroxyurea (hydroxycarbamide); Ifosfamide; Interferon α-2a, α-2b, Lueprolide acetate (LHRH-releasing factor analogue); Lomustine (CCNU); Mechlorethamine HCl (nitrogen mustard); Melphalan; Mercaptopurine; Mesna; Methotrexate (MTX); Mitomycin; Mitotane (o.p'-DDD); Mitoxantrone HCl; Octreotide; Paclitaxel; Plicamycin; Procarbazine HCl; Streptozocin; Tamoxifen citrate; Thioguanine; Thiotepa; Vinblastine sulfate; Vincristine sulfate; Amsacrine (m-AMSA); Azacitidine; Hexamethylmelamine (HMM); Interleukin 2; Mitoguazone (methyl-GAG; methyl glyoxal bis-guanylhydrazone; MGBG); Pentostatin; Semustine (methyl-CCNU); Teniposide (VM-26); paclitaxel and other taxanes; and Vindesine sulfate.

Current methods for the treatment of many neoplastic disorders comprise the use of multiple anti-neoplastic therapeutic agents (i.e., polytherapy). Such polytherapies are known in the art and include, but are not limited to, the combined administration of cyclophosphamide, methotrexate, and 5-fluorouracil for breast cancer; cyclophosphamide, doxorubicin, methotrexate, and procarbazine for non-small cell lung cancer; 5-fluorouracil and levamisole for colon cancer; and, cyclophosphamide, doxorubicin, vincristine, and prednisone for non-Hodgkin's lymphoma. Additional examples of polytherapy regimes useful in the methods of the invention can be found in, for example, DiPiro et al. (1993) *Pharmacotherapy: A Pathophysiological Approach*, $2^{nd}$ ed., Appleton and Lange, Norwalk, Conn.

Additional antineoplastic therapeutic agents which find use in the methods of the present invention include biological response modifiers. As used herein "biological response modifiers" comprise any agent that functions by altering the host response to cancer, rather than by direct cytotoxicity. Biological response modifiers include, for example, monoclonal antibodies and cytokines. See, for example, Isselbacher et al. (1994) *Harrison's Principles of Internal Medicine*, 1834-1841, which is herein incorporated by reference. Cytokines are a group of intercellular messenger proteins that are key immunoregulatory compounds. They comprise the largest group of biologic therapeutics in clinical trials and include interferons (i.e., Type 1 interferons such as INF-α and INF-β and Type II interferons such as INF-γ), interleukins, and hematopoeitic growth factors (i.e., erythropoietin, granulocyte-macrophage colony stimulating factor (GM-CSF) and granulocyte colony stimulating factor (G-CSF)).

As used herein "radiation" is intended to include any treatment of a neoplastic cell or subject by photons, neutrons, electrons, or other type of ionizing radiation. Such radiations include, but are not limited to, X-ray, gamma-radiation, or heavy ion particles, such as alpha or beta particles. Additionally, the radiation may be radioactive. The means for irradiating neoplastic cells in a subject are well known in the art and include, for example, external beam therapy, and brachytherapy.

14-3-3 Antagonists

The present invention provides 14-3-3 antagonists that can either be used alone or in combination with an antineoplastic agent to enhance cell death of a neoplastic cell. The 14-3-3 antagonists useful in the methods of the present invention can comprise a polypeptide having the amino acid sequence of SEQ ID NOS:1 or 2. The polypeptide of SEQ ID NO:1 is a 14-3-3 amphipathic groove binding antagonist referred to herein as "R18". Petosa et al. have demonstrated that the R18 peptide binds 14-3-3 polypeptide within the conserved groove and inhibits the interaction of various 14-3-3 ligands, including for example, Raf-1 kinase and exoenzyme S. ((1998)*J. Biol. Chem.* 273:16305-16310).

Another 14-3-3 antagonist of the present invention comprises the polypeptide of SEQ ID NO:2 and is referred to herein as "difopein". The difopein 14-3-3 antagonist comprises a 62 amino acid polypeptide that comprises two R18 monomers (a.a. 6-25 and 37-56 of SEQ ID NO:2) separated by a non-repeat linker sequence (a.a. 26-36 of SEQ ID NO:2). The 14-3-3 antagonists set forth in SEQ ID NOS:1 and 2 are characterized by their ability to modulate the activity of the 14-3-3 polypeptide (i.e., disrupt 14-3-3 polypeptide/ligand interactions and/or enhance cell death).

Biologically active variants of 14-3-3 antagonists set forth in SEQ ID NOS:1 and 2 are also encompassed by the methods of the present invention. Such variants should retain the biological activity of the 14-3-3 antagonist (i.e., the ability to modulate 14-3-3 activity and thereby disrupt the 14-3-3 polypeptide/ligand interactions, enhance cell death, and/or sensitize the neoplastic cell to an antineoplastic therapeutic agent). Such activity may be measured using standard bioassays. Representative assays detecting the activity of the 14-3-3 antagonists include, for example, various in vitro binding assays as described in Wang et al. (1999) *Biochem.* 38:12499-12504; Petosa et al. (1998) *J. Biol. Chem.* 273:16305-16310; and Wang et al. (1998)*J. Biol. Chem.* 273:16297-16304, all of which are herein incorporated by reference. Further assays that measure cell death include, for example, visual inspection for the morphological signs of cell death, an increase in DNA fragmentation, and an increased activity of polypeptides involved in apoptosis. See, for example, the methods described herein and Zhang et al. (1999) *Proc. Natl. Acad. Sci.* USA 96:8511-8515 and U.S. Pat. No. 5,821,072, all of which are herein incorporated by reference.

Suitable biologically active variants can be fragments, analogues, and derivatives of the 14-3-3 antagonists set forth in SEQ ID NOS:1 and 2. By "fragment" is intended a polypeptide consisting of only a part of the intact 14-3-3 antagonist polypeptide sequence. The fragment can be a C-terminal deletion or N-terminal deletion of the 14-3-3 antagonist polypeptide. By "analogue" is intended an analogue of either the full length polypeptide having biological activity or a fragment thereof, that includes a native sequence and structure having one or more amino acid substitutions, insertions, or deletions. By "derivative" is intended any suitable modification of the 14-3-3 antagonist polypeptide or fragments thereof, or their respective analogues, such as glycosylation, phosphorylation, or other addition of foreign moieties, so long as the activity is retained.

Preferably, naturally or non-naturally occurring variants of a 14-3-3 polypeptide antagonist have amino acid sequences that are at least 70%, preferably 80%, more preferably, 85%, 90%, 91%, 92%, 93%, 94% or 95% identical to the amino acid sequence to the amino acid sequence of SEQ ID NOS:1 or 2 or to a shorter portion of these molecules. More preferably, the molecules are 96%, 97%, 98% or 99% identical. Percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman, *Adv. Appl. Math.* (1981) 2:482-489. A variant may, for example, differ by as few as 1 to 10 amino acid residues, such as 6-10, as few as 5, as few as 4, 3, 2, or even 1 amino acid residue.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 10 contiguous amino acid residues, and may be 12, 13, 14, 15, 16, 17, 18, 20, 25, 30 or more amino acid residues. Corrections for sequence identity associated with conservative residue substitutions or gaps can be made (see Smith-Waterman homology search algorithm).

The art provides substantial guidance regarding the preparation and use of such variants, as discussed further below. A fragment of a 14-3-3 polypeptide antagonist will generally include at least about 10 contiguous amino acid residues of the full-length molecule, preferably about 15-25 contiguous amino acid residues of the full-length 14-3-3 antagonist.

For example, conservative amino acid substitutions may be made at one or more predicted, preferably nonessential amino acid residues. A "nonessential" amino acid residue is a residue that can be altered from the sequence of SEQ ID NOS:1 and 2 without altering its biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Such substitutions would not be made for conserved amino acid residues, or for amino acid residues residing within a conserved motif.

Alternatively, variant 14-3-3 antagonist nucleotide sequences can be made by introducing mutations randomly along all or part of a 14-3-3 antagonist sequence, such as by saturation mutagenesis, and the resultant mutants can be screened for 14-3-3 antagonist activity to identify mutants that retain activity. Following mutagenesis, the encoded polypeptide can be expressed recombinantly, and the activity of the polypeptide can be determined using standard assay techniques described herein.

Alternatively, the 14-3-3 antagonist can be synthesized chemically, by any of several techniques that are known to those skilled in the peptide art. See, for example, Li et al. (1983) *Proc. Natl. Acad. Sci. USA* 80:2216-2220, Steward and Young (1984) *Solid Phase Peptide Synthesis* (Pierce Chemical Company, Rockford, Ill.), and Baraney and Merrifield (1980) *The Peptides: Analysis, Synthesis, Biology*, ed. Gross and Meinhofer, Vol. 2 (Academic Press, New York, 1980), pp. 3-254, discussing solid-phase peptide synthesis techniques; and Bodansky (1984) *Principles of Peptide Synthesis* (Springer-Verlag, Berlin) and Gross and Meinhofer, eds. (1980) *The Peptides: Analysis, Synthesis, Biology*, Vol. 1 (Academic Press, New York), discussing classical solution synthesis. The 14-3-3 antagonist can also be chemically prepared by the method of simultaneous multiple peptide synthesis. See, for example, Houghten (1984) *Proc. Natl. Acad. Sci. USA* 82:5131-5135; and U.S. Pat. No. 4,631,211.

It is further recognized that various other 14-3-3 antagonists known in the art can be used in the methods of the present invention to sensitize a neoplastic cell to an antineoplastic therapeutic agent. Such 14-3-3 antagonists include phosphoserine ligands, such as Raf-1 kinase and Bad which are characterized as having a phosphorylated consensus motif comprising Arg-Ser-Xaa-pSer-Xaa-Pro (SEQ ID NO:3), where 'xaa' represents any residue and pSer is a phosphoserine residue. Examples of such 14-3-3 antagonist are disclosed in U.S. Pat. Nos. 5,948,765; 5,856,445; and 5,597,719; all of which are herein incorporated by reference. Other 14-3-3 antagonists of interest include, for example, IGF-1 receptor (Craparo et al. (1997) *J. Biol. Chem.* 272: 11663-11669), IRSI (Craparo et al. (1997) *J. Biol. Chem.* 272:1663-1669 and Ogihara et al. (1997) *J. Biol. Chem.* 272:25267-25274), the 43 KDa inositol polyphosphate 5-phosphatase (5-phosphatase) (Campbell et al. (1997) *Biochemistry* 36:15363-15370), the glycoprotein Ibα and the exoenzyme S (ExoS) from *Pseudomonas aeruginosa* (Lana et al. (2000) *Biochem. J.* 349:697-701 and Masters et al. (1999) *Biochemistry* 38:5216-5221). All of these references are herein incorporated by reference.

In addition to peptides consisting only of naturally-occurring amino acids, peptidomimetics or peptide analogs are also provided. Peptide analogs are commonly used in the pharmaceutical industry as non-peptide drugs with properties analogous to those of the template polypeptide. These types of non-peptide compound are termed "peptide mimetics" or "peptidomimetics" (Luthman et al. (1996) *A Textbook of Drug Design and Development*, 14:386-406, 2nd Ed., Harwood Academic Publishers; Joachim Grante et al. (1994) *Chem. Int. Ed. Engl.* 33:1699-1720; Fauchere et al. (1986) *Adv. Drug Res.* 15:29; Veber et al. (1985) *TINS*, 392; and Evans et al. (1987) *J. Med. Chem.* 30:1229, all of which are incorporated herein by reference). Peptide mimetics that are structurally similar to therapeutically useful polypeptides may be used to produce an equivalent or enhanced therapeutic or prophylactic effect. Accordingly, additional 14-3-3 antagonists can be identified using techniques known in the art for the development of peptide mimics.

Briefly, these methods involve the identification and characterization of the 14-3-3 polypeptide as well as the 14-3-3 ligand using X-ray crystallography, NMR, or other structure analysis methods such as the DOCK program (Kuntz et al. (1982) *J. Mol. Biol.* 161:269 and Kuntz (1992) *Science* 257:1078) or variants thereof. Potential therapeutic drugs may be designed rationally on the basis on structural information provided thereby. The X-ray crystal structure for the 14-3-3 amphipathic groove binding antagonist, R18 (SEQ ID NO:1), is known (Petosa et al. (1998) *The Journal of Biological Chemistry* 273:16305-16310. Accordingly, a pharmacophore hypothesis can be developed, and compounds subsequently made and tested in an assay system to determine if they are effective 14-3-3 antagonists. The assay system used to characterize the potential 14-3-3 antagonist candidate may be based upon the displacement of a 14-3-3 ligand from the 14-3-3 polypeptide as described elsewhere herein.

Methods of Identifying a 14-3-3 Antagonist

The present invention provides 14-3-3 antagonists comprising the amino acid sequence of SEQ ID NOS:1 and 2. As demonstrated herein, R18 and difopein can be used alone or in combination with an antineoplastic therapeutic agent for the treatment of a neoplastic disorder. These findings indicate that 14-3-3 antagonists find use as therapeutic agents in the treatment of neoplastic disorders. Accordingly, the present invention provides methods for identifying additional 14-3-3 antagonists. Specifically, the present invention provides a method for identifying an agent that selectively inhibits an interaction between a 14-3-3 polypeptide and a 14-3-3 ligand (i.e., a proapoptotic polypeptide).

In one embodiment, the method comprises (a) contacting a 14-3-3 polypeptide with a 14-3-3 antagonist under conditions that permit formation of a 14-3-3/antagonist complex; (b) contacting the 14-3-3/antagonist complex with a candidate agent; and, (c) determining if the candidate agent disrupts the 14-3-3/antagonist complex. A decrease in binding in the presence of the candidate agent compared to that in the absence of a candidate agent indicates that the agent inhibits the direct binding of the 14-3-3 antagonist to the 14-3-3 polypeptide. In this manner, the ability of the candidate agent to compete with the 14-3-3 antagonist for binding is measured. The 14-3-3 antagonist used in the methods of the invention comprises a polypeptide having an amino acid sequence of SEQ ID NO:1, 2, or a biologically active variant thereof.

In another embodiment, the candidate agent is allowed to interact with the 14-3-3 polypeptide. The 14-3-3 polypeptide/candidate agent is subsequently contacted with the 14-3-3 antagonist of SEQ ID NO:1, 2, or a biologically active variant thereof. The ability of the 14-3-3 antagonist to disrupt the 14-3-3 polypeptide/candidate agent is assayed.

Both in vivo and in vitro competitive binding assays are known in the art and can be adapted for use in the methods of the present invention. In vivo assays for 14-3-3 interaction include, for example, the yeast two-hybrid system or a fluorescence resonant energy transfer based assay. In vitro assays include, for example, ELISA/solid phase binding assays, fluorescence polarization based assays, and fluorescence resonant energy transfer assays.

In fluorescence polarization assays, the 14-3-3 antagonist (i.e., SEQ ID NO:1 or 2) is conjugated to a small molecule fluorophore, i.e. fluorescein or Oregon green. Binding of the tagged 14-3-3 antagonist to purified 14-3-3 would cause a decrease in the mobility of the 14-3-3 antagonist and thus, increase the polarization of the emitted light from the fluorophore. This technique thereby allows for the identification of novel 14-3-3 antagonists.

Fluorescence resonant energy transfer uses two fluorescently tagged species, where the emission spectrum of the shorter wavelength tag overlaps the excitation spectrum of the longer wavelength tag. Close proximity of the two molecules induced by binding allows nonradiative excitation of the long wavelength tag when the short wavelength tag is excited. In this method, two DNA constructs coding for the 14-3-3 polypeptide and 14-3-3 antagonist are tagged with (ECFP[])](cyan) and 4EYFP[])](yellow). Upon expression in vivo, energy transfer in the cell lysates can be observed. It is recognized that such assays can be adapted to an in vitro format.

It is further recognized that each of these methods can be adapted for high-throughput screening methods using the 14-3-3 antagonists of the present invention to identify new 14-3-3 antagonists. Hence, the methods of the present invention allow for the high-throughput screening of various candidate agents to identify potentially therapeutically valuable 14-3-3 antagonists. A candidate agent may be a chemical compound, a mixture of chemical compounds, or a biological macromolecule. Such candidate agents can be contained in various agent banks including, for example, compound libraries, peptide libraries, and the like.

Methods of Administration

Delivery of a therapeutically effective amount of a 14-3-3 antagonist may be obtained via administration of a pharmaceutical composition comprising a therapeutically effective dose of this agent. By "therapeutically effective amount" or "dose" is meant the concentration of a 14-3-3 antagonist that is sufficient to elicit the desired therapeutic effect, i.e., the death of a neoplastic cell.

A therapeutically effective amount of a 14-3-3 antagonist when used in combination with an antineoplastic therapeutic agent is sufficient to enhance the death of a neoplastic cell. Accordingly, in this embodiment, an effective amount of the 14-3-3 antagonist augments the clinical outcome of a traditional antineoplastic therapeutic agent. As such, a therapeutically effective dose can be assayed via the sensitization of a neoplastic cell to the antineoplastic therapeutic agent; a decrease in tumor volume; or an increase in cell death. Hence, a therapeutically effective amount is characterized by an improvement in clinical symptoms of a neoplastic disorder and/or a reduction in the effective dosage concentration of the antineoplastic therapeutic agent.

Methods to determine if the neoplastic disorder has been treated are well known to those skilled in the art and include, for example, a decrease in the number of neoplastic cells (ie., a decrease in cell proliferation or a decrease in tumor size). It is recognized that the treatment of the present invention may be a lasting and complete response or can encompass a partial or transient clinical response. See for example, Isselbacher et al. (1996) *Harrison's Principles of Internal Medicine* 13 ed., 1814-1882, herein incorporated by reference.

Assays to test for the sensitization or the enhanced death of neoplastic cells are well known in the art, including, for example, standard dose response assays that assess cell viability; agarose gel electrophoresis of DNA extractions or flow cytometry to determine DNA fragmentation, a characteristic of cell death; assays that measure the activity of polypeptides involved in apoptosis; and assay for morphological signs of cell death. The details regarding such assays are described elsewhere herein. Other assays include, chromatin assays (i.e., counting the frequency of condensed nuclear chromatin) or drug resistance assays as described in, for example, Lowe et al. (1993) *Cell* 74:957-697, herein incorporated by reference. See also U.S. Pat. No. 5,821,072, also herein incorporated by reference.

In addition, assays to test for the sensitization of a neoplastic cell and thereby determine a therapeutically effective dose of a 14-3-3 antagonist alone, or in combination with an antineoplastic therapeutic agent, can be preliminarily evaluated by using a tumor growth regression assay which assesses the ability of tested compounds to inhibit the growth of established solid tumors in mice. The assay can be performed by implanting tumor cells into the fat pads of nude mice. Tumor cells are then allowed to grow to a certain size before the agents are administered. The volumes of tumors are monitored for a set number of weeks, e.g., three weeks. General health of the tested animals is also monitored during the course of the assay.

It is contemplated that the 14-3-3 antagonists of the present invention will be administered to a subject (i.e., a mammal, preferably a human) in therapeutically effective amounts. That is, in an amount sufficient to enhance the death of a neoplastic cell. The effective amount of the 14-3-3 antagonist composition will vary according to the weight, sex, age, and medical history of the subject. Other factors which influence the effective amount may include, but are not limited to, the severity of the patient's condition, the neoplastic disorder being treated, the stability of the 14-3-3 antagonist, and, if desired, the antineoplastic therapeutic agent being administered with the 14-3-3 antagonist. Typically, for a human subject, an effective amount will range from about 0.001 mg/kg of body weight to about 30 mg/kg of body weight. A larger total dose can be delivered by multiple administrations of the agent. Methods to determine efficacy and dosage are known to those skilled in the art. See, for example, Isselbacher et al. (1996) *Harrison's Principles of Internal Medicine* 13 ed., 1814-1882, herein incorporated by reference.

In another embodiment of the invention, the pharmaceutical composition comprising the therapeutically effective dose of a 14-3-3 antagonist is administered intermittently. By "intermittent administration" is intended administration of a therapeutically effective dose of a 14-3-3 antagonist, followed by a time period of discontinuance, which is then followed by another administration of a therapeutically effective dose, and so forth. Administration of the therapeutically effective dose may be achieved in a continuous manner, as for example with a sustained-release formulation, or it may be achieved according to a desired daily dosage regimen, as for example with one, two, three, or more administrations per day. By "time period of discontinuance" is intended a discontinuing of the continuous sustained-released or daily administration of the 14-3-3 antagonist. The time period of discontinuance may be longer or shorter than the period of continuous sustained-release or daily administration. During the time period of discontinuance, the 14-3-3 antagonist level in the relevant tissue is substantially below the maximum level obtained during the treatment. The preferred length of the discontinuance period depends on the concentration of the effective dose and the form of 14-3-3 antagonist used. The discontinuance period can be at least 2 days, at least 4 days or at least 1 week. In other embodiments, the period of discontinuance is at least 1 month, 2 months, 3 months, 4 months or greater. When a sustained-release formulation is used, the discontinuance period must be extended to account for the greater residence time of the 14-3-3 antagonist at the site of injury. Alternatively, the frequency of administration of the effective dose of the sustained-release formulation can be decreased accordingly. An intermittent schedule of administration of 14-3-3 antagonist can continue until the desired therapeutic effect, and ultimately treatment of the neoplastic disease or disorder is achieved.

It is recognized that the 14-3-3 antagonist and the antineoplastic therapeutic agent can be administered in a fixed combination (i.e., a single pharmaceutical formulation that contains both active materials). Alternatively, the 14-3-3 antagonist may be administered simultaneously with the antineoplastic therapeutic agent. In another embodiment, the 14-3-3 antagonist and the antineoplastic therapeutic agent are administered sequentially (i.e., administration of the 14-3-3 antagonist begins shortly after the end of the antineoplastic therapeutic agent regime or, alternatively, administration of the 14-3-3 antagonist precedes the administration of the antineoplastic therapeutic agent). One of skill in the art will recognized that the most preferred method of administration will allow the desired therapeutic effect, i.e., the enhanced cell death of a neoplastic cell.

All conventional forms of administration of the 14-3-3 antagonist and the antineoplastic may be used (i.e., tablets, capsules, dragees, syrups, solutions and suspensions) for the methods of the present invention. Preferred forms of systemic administration of the pharmaceutical compositions include injection, typically by intravenous injection. Other injection routes, such as subcutaneous, intramuscular, or intraperitoneal can also be used. Alternative means for systemic administration include transmucosal and transdermal administration using penetrates such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The 14-3-3 antagonists of the present invention may be dissolved in any physiologically tolerated liquid in order to prepare an injectable bolus. It is generally preferable to prepare such a bolus by dissolving the molecule in normal saline.

It is further recognized that when the 14-3-3 antagonist of choice is a polypeptide, the antagonist can be administered to the neoplastic cell using conventional gene therapy techniques. In such instances, the nucleotide sequence encoding the 14-3-3 antagonist is operably linked to a promoter that is active in the targeted neoplastic cell. The DNA construct containing the 14-3-3 antagonist is subsequently inserted into a vector and introduced in the subject.

Pharmaceutical Compositions

The present invention also provides pharmaceutical formulations or compositions, both for veterinary and for human medical use, which comprise a 14-3-3 antagonist alone or in combination with one or more pharmaceutically acceptable carriers. In additional embodiments, the pharmaceutical compositions comprising the 14-3-3 antagonist further comprise an antineoplastic therapeutic agent. The carrier(s) must be pharmaceutically acceptable in the sense of being compatible with the other ingredients of the formulation and not unduly deleterious to the recipient thereof.

The 14-3-3 antagonist compositions can be formulated according to known methods to prepare pharmaceutically useful compositions, such as by admixture with a pharmaceutically acceptable carrier vehicle. Suitable vehicles and their formulation are described, for example, in *Remington's Pharmaceutical Sciences* (16th ed., Osol, A. (ed.), Mack, Easton Pa. (1980)). A pharmaceutically acceptable composition suitable for effective administration will contain an effective amount of the 14-3-3 antagonist. Additional pharmaceutical methods may be employed to control the duration of action. Controlled release preparations may be achieved by the use of polymers to complex or absorb the 14-3-3 antagonist. The controlled delivery may be exercised by selecting appropriate macromolecules (for example, polyesters, polyamino acids, polyvinyl pyrrolidone, ethylene-vinylacetate, hydrogels, poly(lactic acid) methylcellulose, carboxymethylcellulose, or protamine sulfate). Altering the concentration of such macromolecules may also control the rate of drug release.

Alternatively, it is possible to entrap the therapeutic agents in microcapsules prepared, for example, by coacervation techniques or by interfacial polymerization, for example, by the use of hydroxymethyl cellulose or gelatin-microcapsules or poly(methylmethacrylate) microcapsules, respectively, or in a colloid drug delivery system, for example, liposomes, albumin, microspheres, microemulsions, nanoparticles, nanocapsules, or in macroemulsions. Such teachings are disclosed in *Remington's Pharmaceutical Sciences* (1980), herein incorporated by reference.

Articles of Manufacture

The present invention also includes an article of manufacture providing a 14-3-3 antagonist. The article of manufacture may contain the 14-3-3 antagonist alone or in combination with an antineoplastic therapeutic agent. The article of manufacture can include a vial or other container that contains a composition suitable for the present method together with any carrier, either dried or in liquid form. The article of manufacture further includes instructions in the form of a label on the container and/or in the form of an insert included in a box in which the container is packaged, for the carrying out the method of the invention. The instructions can also be printed on the box in which the vial is packaged. The instructions contain information such as sufficient dosage and administration information so as to allow the subject or a worker in the field to administer the pharmaceutical composition. It is anticipated that a worker in the field encompasses any doctor, nurse, technician, spouse, or other caregiver that might administer the composition. The pharmaceutical composition can also be self-administered by the subject.

Having now generally described this invention, the same will be better understood by reference to certain specific examples which are included herein for purposes of illustration only, and are not intended to be limiting of the invention, unless specified.

EXPERIMENTAL

EXAMPLE 1

R18 is a 14-3-3 Antagonist that Disrupts 14-3-3/Ligand Interactions

To control 14-3-3/ligand interactions, the interaction of the 14-3-3 antagonist, R18, with the 14-3-3 polypeptide was characterized. The R18 polypeptide (SEQ ID NO:1) was isolated from a phage display library based on its affinity for 14-3-3 proteins. It appears that this peptide binds different isoforms of the 14-3-3 with similar affinity (KD=80 nM), thus it may serve as a general 14-3-3 inhibitor. Importantly R18 exhibited high specificity for 14-3-3 proteins. See, for example, Wang et al. (1999) *Biochemistry* 38:12499-12504.

To determine the effectiveness of various 14-3-3 antagonist, including R18, S-Raf259, and pS-Raf-259, the peptide antagonists were preincubated with immobilized His-14-3-3ζ before adding [$^{35}$S]-labeled ASK1. After washing, 14-3-3-bound ASK1 was quantified by PhosphorImager. The percentage of ASK1 bound to 14-3-3 relative to peptide-free samples is plotted against increasing concentration of the test peptides (FIG. 1). R18 has a potent inhibitory affect on the interaction of 14-3-3ζ with ASK1. The phosphorylated peptide pS-Raf-259 that interacts at the amphipathic groove of the 14-3-3 polypeptide was also an effective antagonist. However, as shown in FIG. 1, the R18 antagonist has a stronger inhibitory affect on 14-3-3ζ/ASK1 than the phosphorylated pS-Raf-259 polypeptide.

Figure 2:
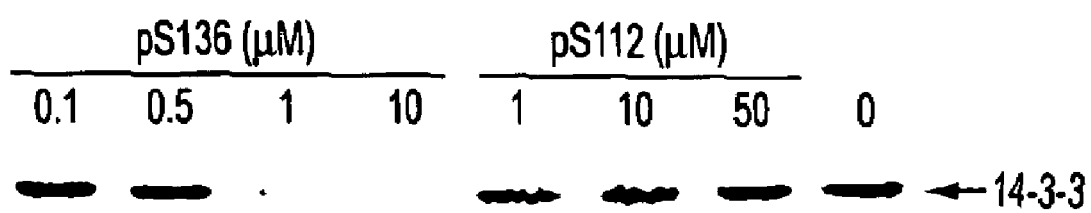
FIG. 2 demonstrates that the 14-3-3 antagonist R18 competes with a Bad derived peptide for 14-3-3 binding.

FIG. 2 demonstrates that the R18 antagonist (SEQ ID NO:1) competes with a Bad derived peptide for 14-3-3 binding. R18 was covalently coupled to Sepharose beads. The beads were then incubated with 100 nM 14-3-3ζ dimer along with the indicated concentrations of synthetic phosphopeptides derived from Bad. pS136 contains a 14-3-3 binding site, while pS112 is a similar peptide incapable of binding 14-3-3. Unbound 14-3-3 was washed away from the beads and the remaining proteins were visualized by SDS-PAGE and sliver staining. The data demonstrates that the R18 polypeptide of SEQ ID NO:1 competes with a Bad derived peptide for 14-3-3 binding. See also, Masters et al. (2001) *Molecular Pharmacology* 60: 1325-1331, herein incorporated by reference.

Figure 3:
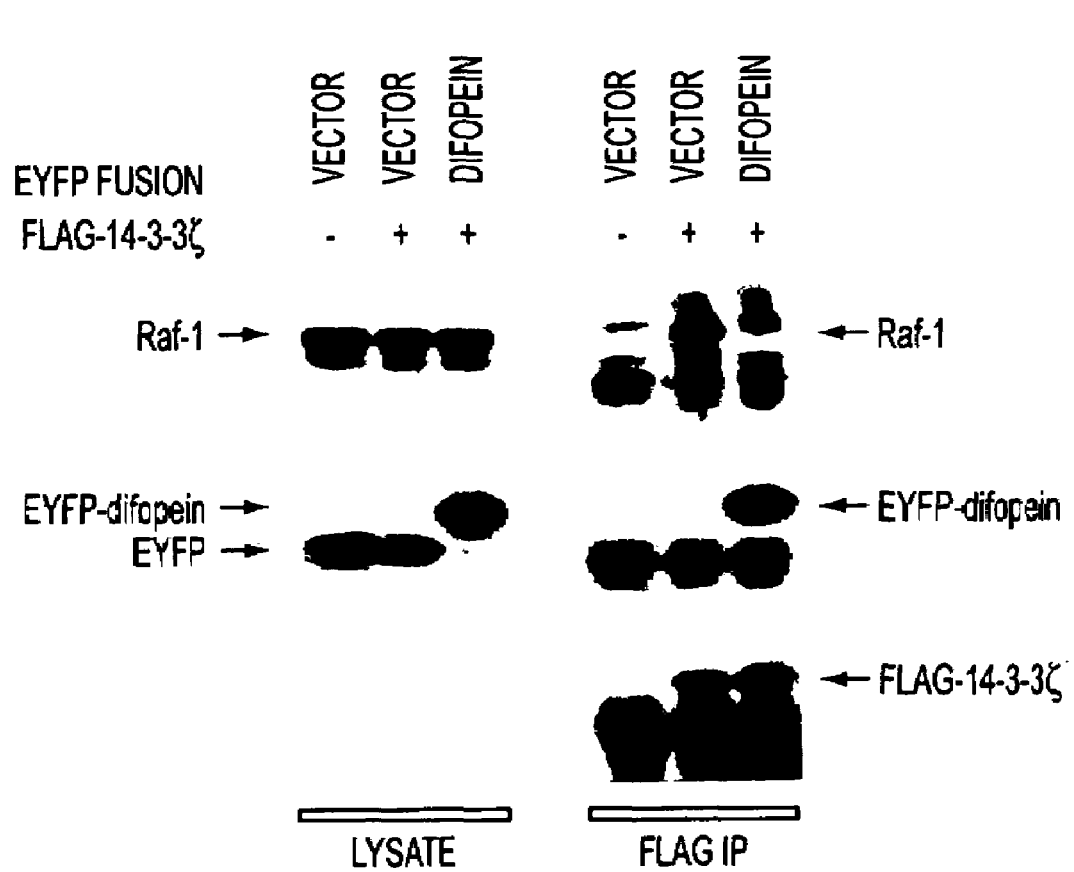
FIG. 3 demonstrates that the 14-3-3 antagonist difopein can bind 14-3-3 in vivo and can disrupt the interaction of the 14-3-3 polypeptide with endogenous Raf-1.

Difopein is a 62 amino acid polypeptide having 14-3-3 antagonist activity. The amino acid sequence of difopein is shown in SEQ ID NO:2 and comprises two R18 monomers (amino acids 6-25 and 37-56 of SEQ ID NO:2) separated by non-repeat linker sequences (amino acids 26-36 of SEQ ID NO:2). FIG. 3 demonstrates that difopein can bind 14-3-3 in vivo and can disrupt the interaction of 14-3-3 with Raf-1. Specifically, HEK293 cells were transfected with DNA coding for FLAG-tagged 14-3-3ζ and either EYFP or EYFP-difopein as indicated. 14-3-3 was immunoprecipitated using anti-FLAG (M2; Sigma Chemical Co.). In the presence of EYFP, 14-3-3ζ was able to co-precipitate endogenous Raf-1. However, EYFP-difopein blocked co-precipitation of Raf-1 and instead was itself pulled down by 14-3-3. Thus, difopein can bind 14-3-3 in vivo and this binding can competitively disrupt the binding of 14-3-3 to ligands known to interact in the amphipathic groove of 14-3-3. See also, Masters et al. (2001) *Journal of Biological Chemistry* 276: 45193-45200, herein incorporated by reference.

EXAMPLE 2

Disruption of 14-3-3/Ligand Interactions Decreases Cell Viability

Figure 4:
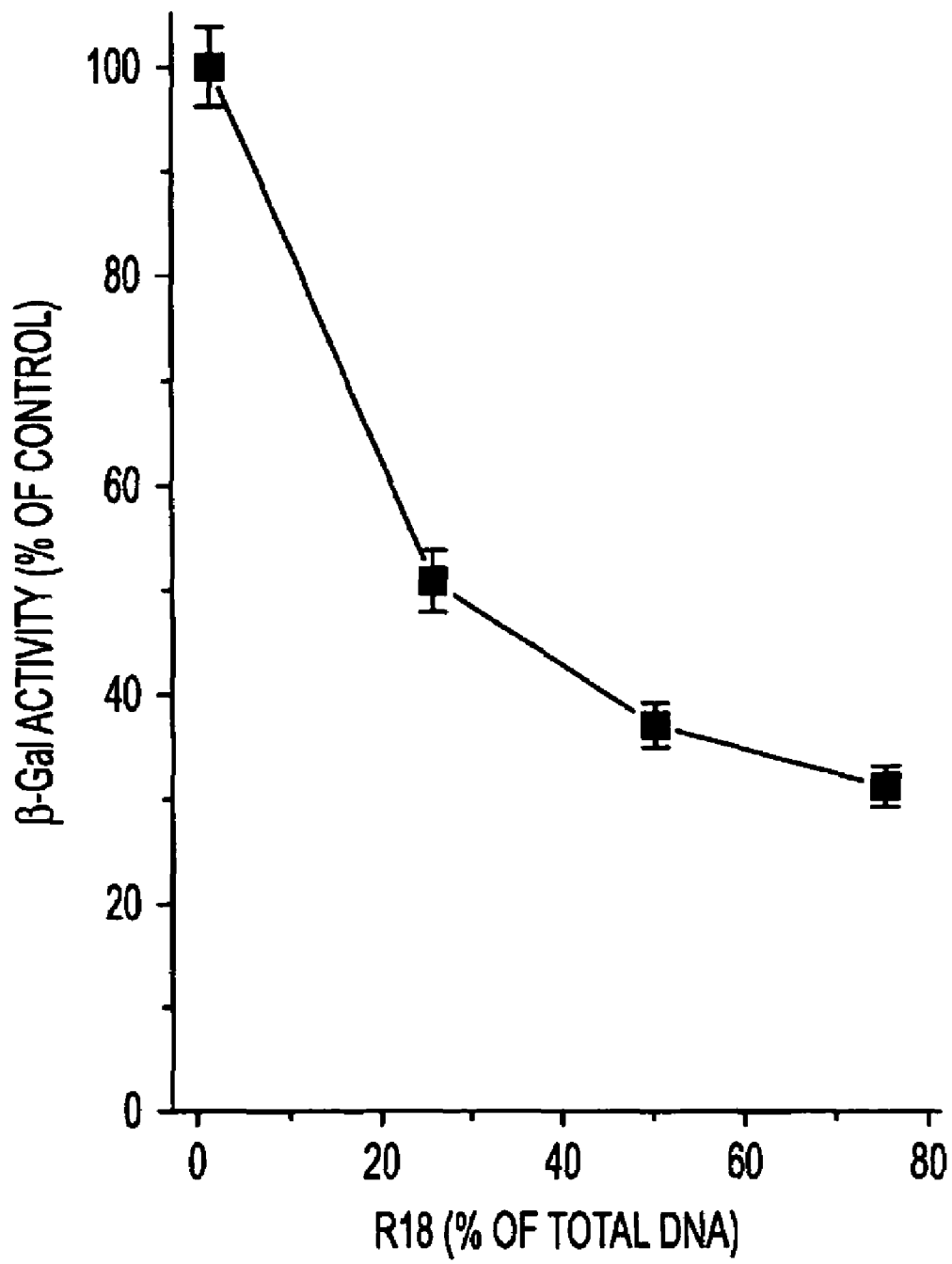
FIG. 4 demonstrates that the 14-3-3 antagonist R18 can induce cell death in a dose dependent fashion.

FIG. 4 shows the result from an attachment based viability assay in COS-7 cells. R18 is placed under the control of the CMV promoter in a mammalian expression vector pCR3.1 (pSCM110). Cells expressing the control pcDNA3 along with a lacZ marker gave high β-gal activity that was set as 100% survival. Expression of R18 drastically decreased the population of viable cells, as shown by diminished β-gal activity. The R18 effect was dose-dependent because increased R18 expression was correlated with decreased cell viability. Because of the high affinity of R18 for the 14-3-3 polypeptide and the interaction of R18 at the amphipathic binding groove, the decreased cell viability is likely due to R18 induced disruption of 14-3-3 ligand interactions. This data supports the notion that 14-3-3/ligand interactions are essential for cell survival. It appears that R18 induces cell death by an annexin V-positive phenotype, an early marker for apoptosis (data not shown).

Figure 5:
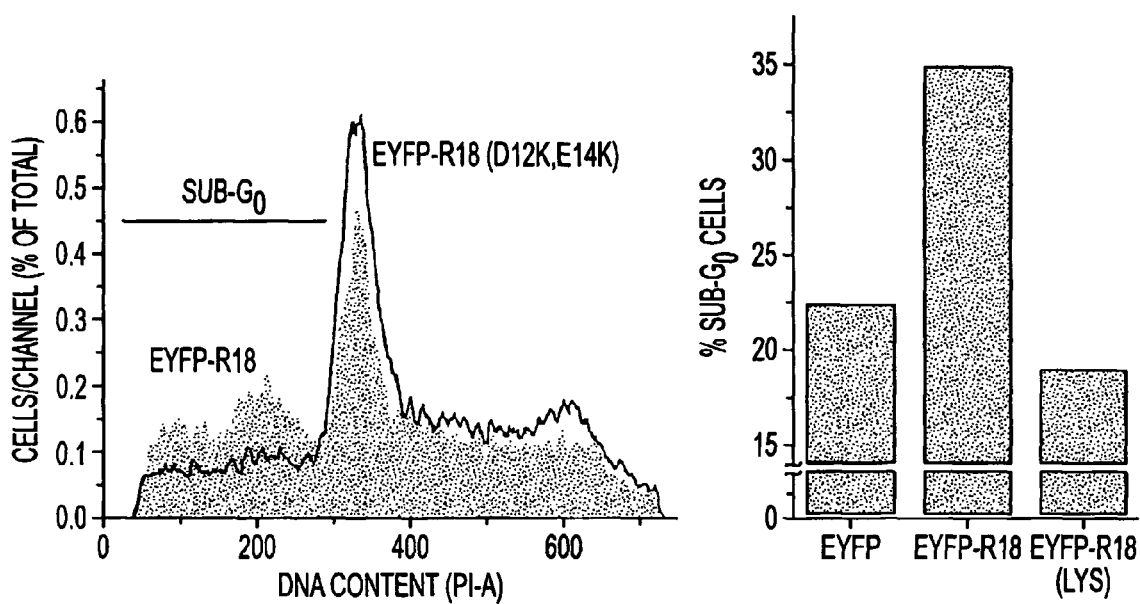
FIG. 5 demonstrates that the cell death induced by the 14-3-3 antagonist R18 is dependant on the acidic residues that interact with the 14-3-3 polypeptide.

FIG. 5 demonstrates cell death induced by the R18 antagonist of SEQ ID NO:1 is dependant on acidic 14-3-3 interacting residues. The two acidic residues of R18 (Asp and Glu) which are involved in coordinating the basic cluster of 14-3-3 were changed to lysine. This peptide is not expected to bind 14-3-3, but it could retain interaction with other cellular partners if they do exist. Cos-7 cells were cotransfected with a farnesylated (EGFP[)] marker along with EYFP, EYFP-R18, or EYFP-R18 (D12K,E14K). After 24 hours, cells were fixed in ethanol and DNA was stained with propidium iodide. EGFP and PI signal intensities were measured on a FACScan flow cytometer (Becton Dickinson), and transfected cells were placed in various phases of the cell cycle based on their DNA content. R18 caused an increase in the fraction of cells containing less than normal amounts of DNA (sub $G_0$), which is consistent with DNA fragments caused by apoptosis. R18 (D12K, E14K), which has charge reversals at two of the residues known to interact with 14-3-3, was unable to induce cell death, which argues that the R18 induced death was caused by its ability to bind and inhibit 14-3-3.

The second approach used a 14-3-3 binding molecule that is structurally unrelated to difopein, which should therefore have a different spectrum of non-14-3-3 specific protein interactions. We have characterized the phosphorylation-independent interaction of 14-3-3 with *Pseudomonas aeruginosa* exoenzyme S finding that it binds in the amphipathic groove of 14-3-3 with high affinity. See, for example, Masters et al. (1999) *Biochemistry* 38:5216-5221 and Zhang et al. (1997) *J. Biol. Chem.* 272:13717-13724. Others later determined that the 14-3-3 binding epitope of exoenzyme S is localized to its C-terminal 54 residues (Henriksson et al. (2000) *Biochem* 349:697-701). This domain, termed C54, was able to bind 14-3-3 and induce apoptosis in COS-7 cells as determined by DNA content (data not shown). Thus, a strong correlation exists between the abilities of these molecules to bind 14-3-3 and to cause cell death. This argues that the apoptosis caused by difopein is due to inhibition of 14-3-3/ligand interactions and that 14-3-3, by binding other cellular proteins, mediates a critical prosurvival signal.

Figure 6:
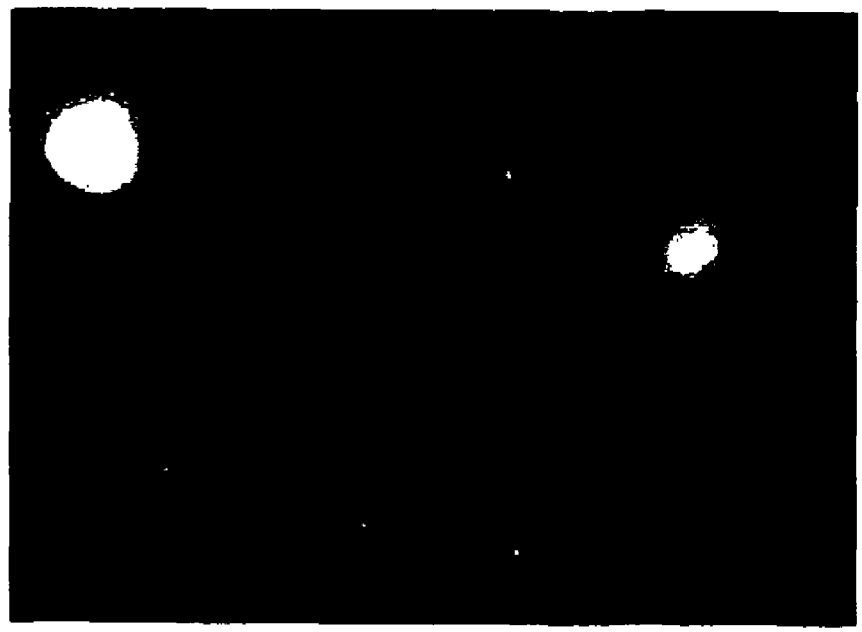
FIG. 6 shows the 14-3-3 antagonist difopein is distributed through out the cell.
Figure 6:
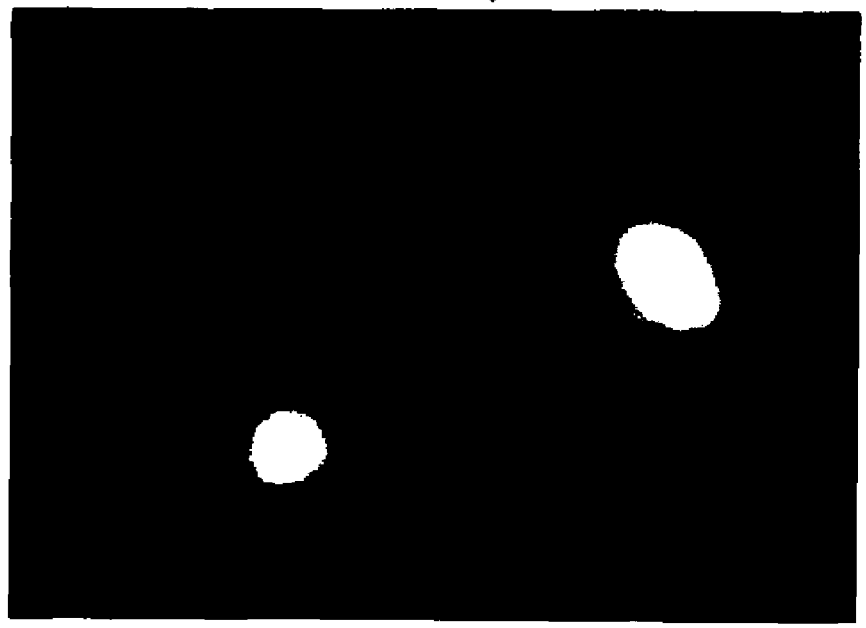
Figure 7:
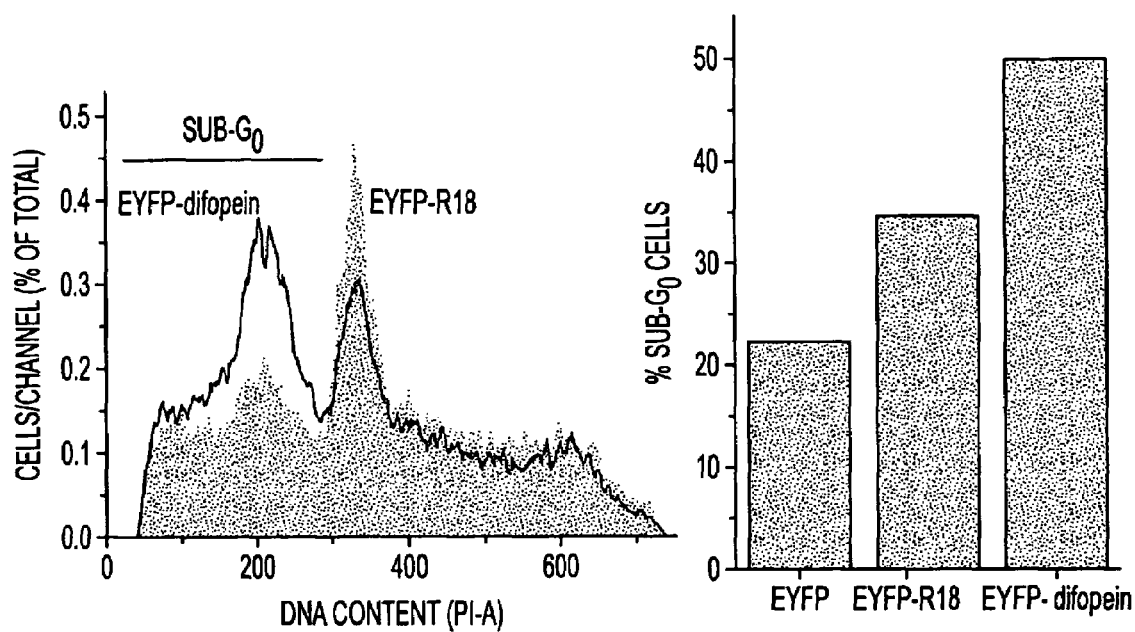
FIG. 7 demonstrates that diamerization of R18 enhances its ability to kill cells.

Studies further demonstrate that the difopein antagonist is distributed through out the cell. EYFP or EYFP-difopein was transfected into Cos-7 cells. Approximately 24 hours after transfection cells were fixed with 4% paraformaldehyde and visualized by fluoresence microscopy. As shown in FIG. 6, EYFP-difopein was found throughout the cells and its distribution appeared identical to that of EYFP. Cos-7 cells were assayed for cell death using EYFP-tagged R18 or a dimerized form of R18 (difopein). Because 14-3-3 exists in vivo as a dimer, dimerization of 14-3-3 ligands is expected to increase their affinity for 14-3-3. As shown in FIG. 7, difopein dramatically enhanced the cell death as compared to monomeric R18, and thus it was used for many of the subsequent studies.

Figure 8A:
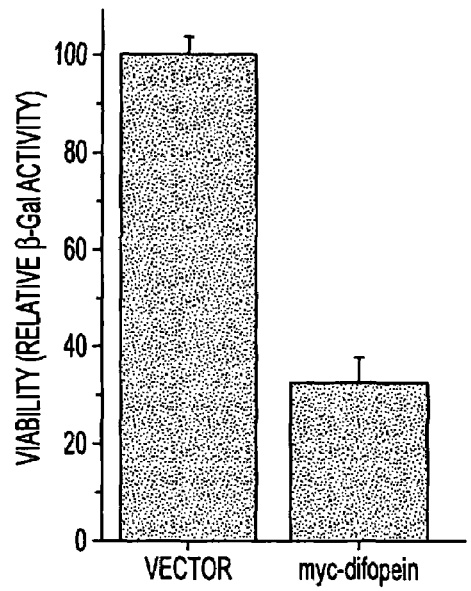
FIG. 8 demonstrates that the 14-3-3 antagonist difopein can induce apoptotic cell death.

Further studies were preformed to demonstrate that difopein induces cell death. In FIG. 8a, Cos-7 cells were co-transfected with myc-tagged difopein or a control vector along with a lacZ reported gene. After approximately 48 hours floating cells were gently washed away and attached cells were lysed and assayed for β-galactosidase. Decreased β-gal activity indicated a loss of viability. As shown in FIG. 8a, expression of difopein decreased β-gal activity, an indication of a loss of cell viability.

Figure 8B:
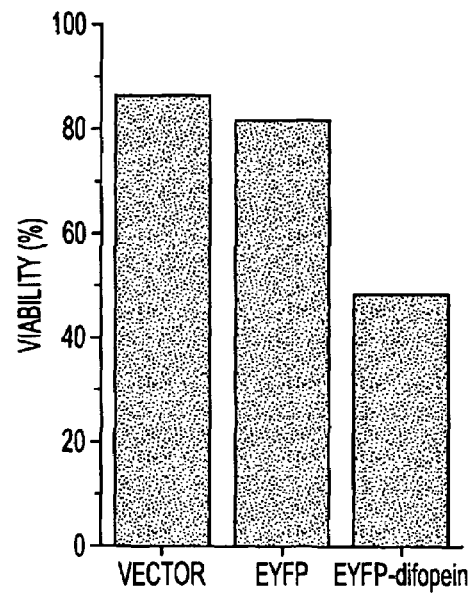
Figure 8C:
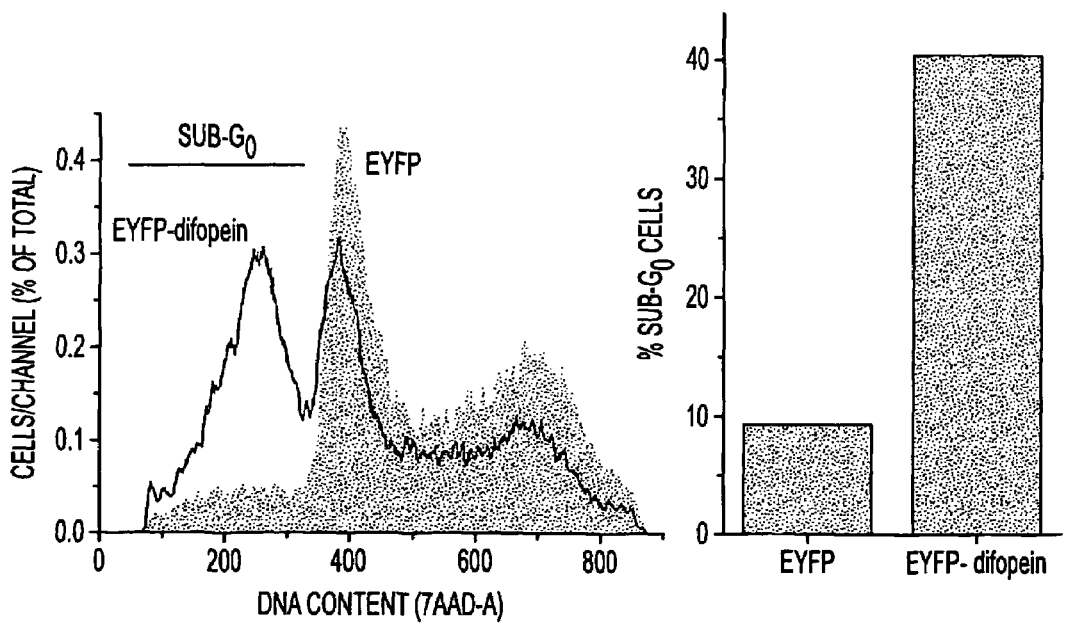

In another assay, Cos-7 cells were cotransfected with a lacZ marker in addition to any EYFP-difopein fusion, EYFP alone, or empty vector. Approximately 24 hours post transfection, cells were fixed and transfected cells were identified by staining with X-gal. Viability of the transfected cells was determined by microscopic examination of cell morphology: live cells were flat, while dead cells were rounded up. As shown in FIG. 8b, EYFP expression had no effect on viability, but the EYFP-difopein fusion reduced the live cell population by about one-half In yet another assay, (FIG. 8c) Cos-7 cells were transfected with EYFP or EYFP-difopein as indicated, and cell death was determined as in FIG. 5. Internucleosomal DNA cleavage, which is a commonly used marker of apoptosis, produces small fragments that can diffuse out of cells during ethanol fixation resulting in decreased signals being seen on staining for DNA (Sub-$G_0$ DNA content). Therefore, the appearance of cell containing sub $G_0$ levels of DNA indicates apoptotic cell death. When sub $G_0$ cells were excluded from analysis (not shown), no significant difference in DNA content distribution was seen between EYFP and EYFP-difopein, suggesting that difopein does not disrupt the cell cycle.

It is possible that the effects of 14-3-3 inhibition on apoptosis are restricted to COS-7 cells. Three additional cell lines were used to examine this issue: A549 lung cancer cells, DU145 prostate cancer cells, and HeLa cervical carcinoma cells. In the attachment-based viability assay, Myc-difopein was found to kill all three of these cell lines to varying degrees (data not shown), supporting the generality of the difopein effect. Because 14-3-3 proteins are ubiquitously expressed and because 14-3-3 can potentially target many different apoptosis regulating molecules, we anticipate that most cells will show some degree of sensitivity to 14-3-3 inhibitors.

Figure 9:
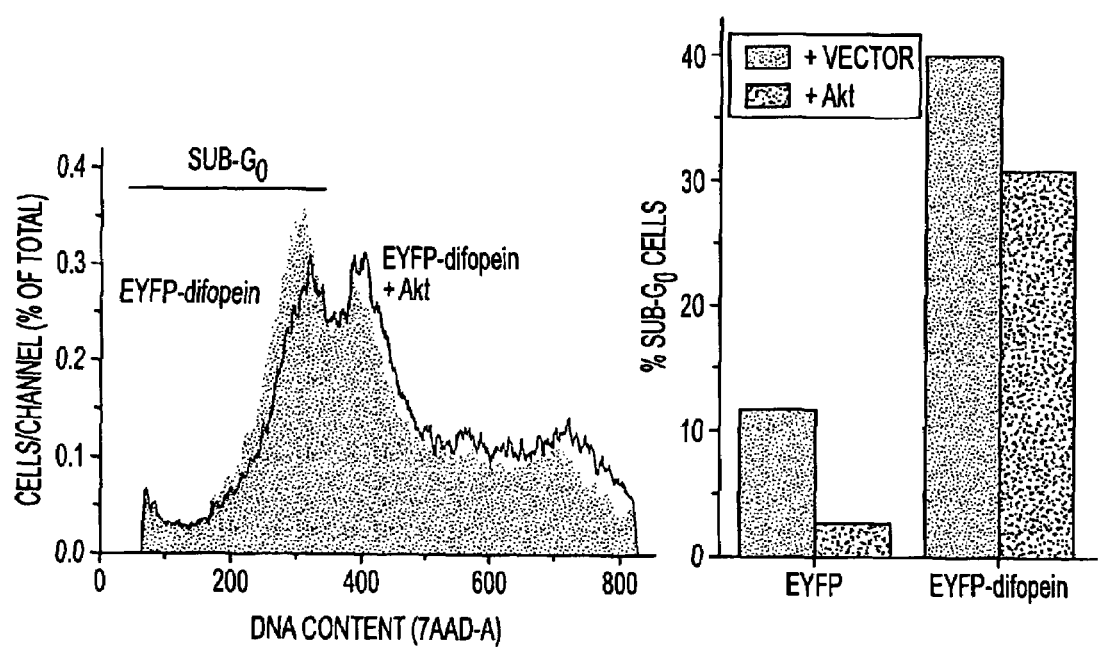
FIG. 9 demonstrates that the 14-3-3 antagonist difopein kills cells through an Akt independent pathway.

FIG. 9 demonstrates that difopein kills cells through an Akt independent pathway. Cos-7 cells were assayed as in FIG. 5 except that a vector expressing a constitutively active form of Akt was included. Difopein induced cell death is relatively insensitive to Akt expression. The Akt proto-oncogene acts on several targets to prevent cell death. This result supports the idea that difopein can be used to treat cancer cells that have lost their sensitivity to apoptosis as a result of increased activity of prosurvival signaling networks.

Figure 10A:
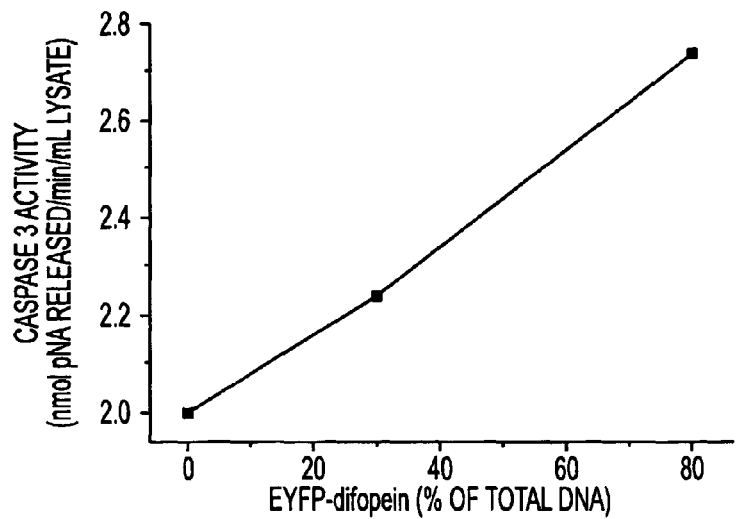
FIG. 10 demonstrates that difopein induced cell death is caspase dependant.
Figure 10B:
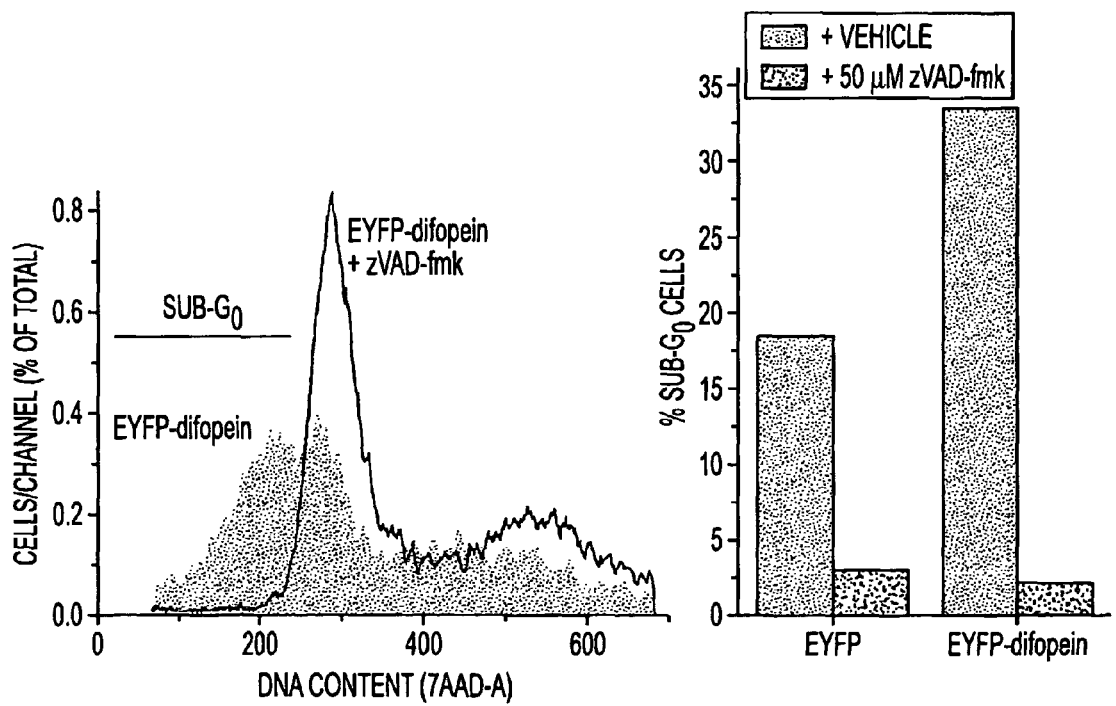

FIG. 10 demonstrates difopein induced cell death is caspase dependent. Cos-7 cells were lysed 12 hours after transfection with various amounts of DNA coding for EYFP-difopein. Equal amounts of lysates were assayed for the ability to liberate p-nitroaniline (pNA) from the caspase 3 substrate Ac-DEVD-pNA. As shown in FIG. 10a, expression of EYFP-difopein led to a dose dependent increase in pNA release that was completely blocked by the caspase 3 inhibitor Ac-DEVD-CHO. In another study, Cos-7 cells were assayed as in FIG. 5, except that they were treated with 50 µM of the pan-caspase inhibitor zVAD-fink or vehicle immediately prior to transfection (FIG. 10b). As caspases are critical downstream effectors of numerous apoptotic stimuli, these results strongly support the hypothesis that difopein kills cells through apoptosis.

EXAMPLE 3

14-3-3 Antagonists Sensitize Tumor Cells to Cisplatin-mediated Cell Death

Figure 11A:
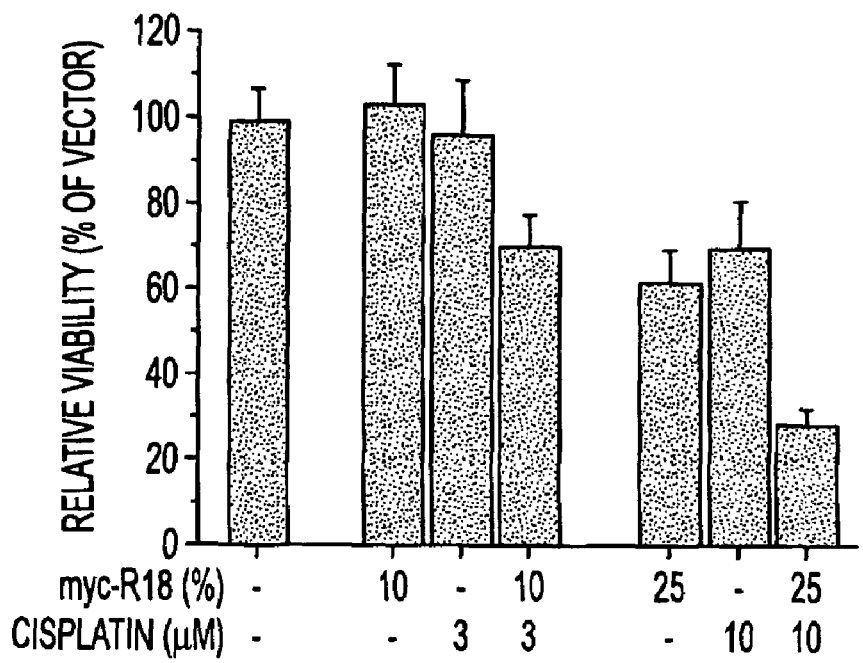
FIG. 11 demonstrates that the inhibition of 14-3-3 polypeptide/ligand interactions can enhance the ability of chemotherapeutic agents to kill cells.
Figure 11B:
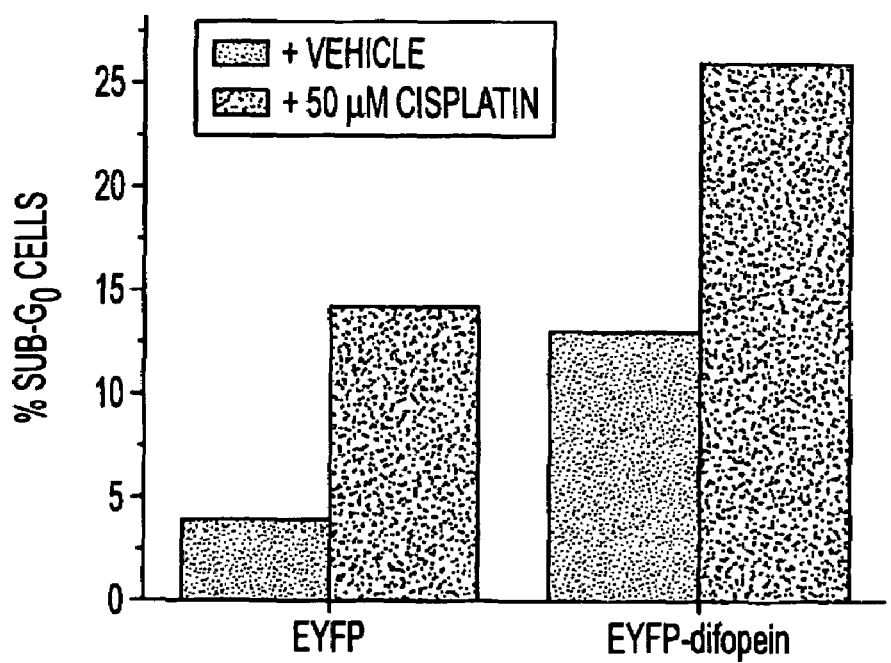

Inhibition of 14-3-3/ligand interactions may facilitate apoptotic cell death induced by cytotoxic agents. To test this possibility, the effects of expression of R18 and difopein on cisplatin-induced cell death was examined (FIG. 11). In FIG. 11a, Cos-7 cells were transfected with a lacZ marker gene along with myc-tagged R18 DNA (amount used shown as the fraction of total DNA). 12 hours after transfection, the indicated concentrations of cisplatin were added. Approximately 36 hours later the viability of the cells was determined as in FIG. 3 above. In FIG. 11b, HeLa cervical cancer cells were transfected with EYFP or EYFP-difopein as indicated. 24 hours later, 50 µM cisplatin or vehicle was added. After 24 hours of cisplatin treatment, the cells were assayed as in 2 above. These data shown in FIGS. 11a and b demonstrate that the R18 and difopein 14-3-3 antagonist can enhance the ability of an antineoplastic drug to kill cells.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of enhancing the death of a neoplastic cell in vitro comprising providing to said neoplastic cell a therapeutically effective amount of a 14-3-3 antagonist and at least one antineoplastic therapeutic agent, wherein said 14-3-3 antagonist is a 14-3-3 amphipathic groove binding antagonist, and wherein said 14-3-3 antagonist is selected from the group consisting of:
   a) an amino acid sequence having at least 80% sequence identity across the entirety of SEQ ID NO:2, wherein said sequence disrupts the interaction between a 14-3-3 polypeptide and a 14-3-3 ligand and,
   b) an amino acid sequence having at least 25 contiguous amino acids of SEQ ID NO:2, wherein said sequence disrupts the interaction between a 14-3-3 polypeptide and a 14-3-3 ligand;
   wherein said enhancement is relative to the death of a neoplastic cell by administration of either of said antineoplastic agent or said 14-3-3 antagonist alone.

2. The method of claim 1, wherein the 14-3-3 antagonist directly interacts with a 14-3-3 polypeptide.

3. The method of claim 1, wherein said antineoplastic therapeutic agent is a chemotherapeutic agent.

4. The method of claim 3, wherein said chemotherapeutic agent is selected from the group consisting of etoposide, cisplatin, doxorubicin, paclitaxel, methotrexate, and 5-fluorouracil.

5. The method of claim 1, wherein said antineoplastic therapeutic agent is a radiation.

6. The method of claim 1, wherein said 14-3-3 antagonist comprises SEQ ID NO:2.

7. The method of claim 1, wherein the 14-3-3 antagonist and the antineoplastic therapeutic agent are provided to the cell sequentially.

8. The method of claim 1, wherein the 14-3-3 antagonist and the antineoplastic therapeutic agent are provided to the cell simultaneously.

9. The method of claim 1, wherein said neoplastic cell is a mammalian cell.

10. The method of claim 9, wherein said mammalian cell is a human cell.

11. A composition comprising a therapeutically effective amount of a 14-3-3 antagonist and at least one antineoplastic therapeutic agent, wherein said 14-3-3 antagonist is a 14-3-3 amphipathic groove binding antagonist, and wherein said 14-3-3 antagonist is selected from the group consisting of:
   a) an amino acid sequence having at least 80% sequence identity across the entirety of SEQ ID NO:2, wherein said sequence disrupts the interaction between a 14-3-3 polypeptide and a 14-3-3 ligand; and,
   b) an amino acid sequence having at least 25 contiguous amino acids of SEQ ID NO:2, wherein said sequence disrupts the interaction between a 14-3-3 polypeptide and a 14-3-3 ligand.

12. The composition of claim 11, wherein said antineoplastic therapeutic agent is a chemotherapeutic agent, a biological response modifier, or a radiation.

13. The composition of claim 12, wherein said chemotherapeutic agent is selected from the group consisting of etoposide, cisplatin, doxorubicin, paclitaxel, methotrexate, and 5-fluorouracil.

14. The composition of claim 11, wherein the 14-3-3 antagonist directly interacts with a 14-3-3 polypeptide.

15. The composition of claim 11, wherein said 14-3-3 antagonist comprises SEQ ID NO:2.

16. A method of identifying an agent that selectively inhibits an interaction between a 14-3-3 polypeptide and a 14-3-3 ligand comprising:
   a) contacting a 14-3-3 polypeptide with a 14-3-3 antagonist under conditions that permit formation of a 14-3-3/antagonist complex, said 14-3-3 antagonist comprises a polypeptide having an amino acid sequence selected from the group consisting of:
      i) an amino acid sequence set forth in SEQ ID NO:2;
      ii) an amino acid sequence having at least 80% sequence identity across the entirety of SEQ ID NO:2, wherein said sequence disrupts an interaction between a 14-3-3 polypeptide and a 14-3-3 ligand; and,
      iii) an amino acid sequence having at least 25 contiguous amino acids of SEQ ID NO:2, wherein said sequence disrupts an interaction between a 14-3-3 polypeptide and a 14-3-3 ligand;
   b) contacting said 14-3-3/antagonist complex with a candidate agent; and,
   c) determining if the candidate agent disrupts the 14-3-3/antagonist complex.

17. A method of identifying an agent that selectively inhibits an interaction between a 14-3-3 polypeptide and a 14-3-3 ligand comprising:
   a) contacting a 14-3-3 polypeptide with a candidate agent under conditions that allow for a 14-3-3/candidate agent complex to form;
   b) contacting said 14-3-3/candidate agent complex with a 14-3-3 antagonist, said 14-3-3 antagonist comprises a polypeptide having an amino acid sequence selected from the group consisting of:
      i) an amino acid sequence set forth in SEQ ID:2;
      ii) an amino acid sequence having at least 80% sequence identity across the entirety of SEQ ID NO:2, wherein said sequence disrupts an interaction between a 14-3-3 polypeptide and a 14-3-3 ligand; and,
      iii) an amino acid sequence having at least 25 contiguous amino acids of SEQ ID NO:2, wherein said sequence disrupts an interaction between a 14-3-3 polypeptide and a 14-3-3 ligand; and,
   c) determining if the 14-3-3 antagonist disrupts the 14-3-3/candidate agent complex.

18. The method according to claims 16 or 17, wherein said method occurs in vivo or in vitro.

19. An isolated polypeptide comprising an amino acid sequence selected from the group consisting of:
   a) an amino acid sequence set forth in SEQ ID NO:2;
   b) an amino acid sequence having at least 80% sequence identity across the entirety of SEQ ID NO:2, wherein the sequence disrupts the interaction of a 14-3-3 ligand with a 14-3-3 polypeptide; and,
   c) an amino acid sequence having at least 25 contiguous amino acids of SEQ ID NO:2, wherein the sequence disrupts the interaction of a 14-3-3 ligand with a 14-3-3 polypeptide.

* * * * *

SEQUENCE LISTING

<160> NUMBER OF SEQ ID NOS: 3

<210> SEQ ID NO 1
<211> LENGTH: 20
<212> TYPE: PRT
<213> ORGANISM: Artificial Sequence
<220> FEATURE:

```
<223> OTHER INFORMATION: R18 polypeptide sequence

<400> SEQUENCE: 1

Pro His Cys Val Pro Arg Asp Leu Ser Trp Leu Asp Leu Glu Ala Asn
1               5                   10                  15

Met Cys Leu Pro
            20

<210> SEQ ID NO 2
<211> LENGTH: 62
<212> TYPE: PRT
<213> ORGANISM: Artificial Sequence
<220> FEATURE:
<223> OTHER INFORMATION: difopein  polypeptide sequence

<400> SEQUENCE: 2

Ser Ala Asp Gly Ala Pro His Cys Val Pro Arg Asp Leu Ser Trp Leu
1               5                   10                  15

Asp Leu Glu Ala Asn Met Cys Leu Pro Gly Ala Ala Gly Leu Asp Ser
            20                  25                  30

Ala Asp Gly Ala Pro His Cys Val Pro Arg Asp Leu Ser Trp Leu Asp
        35                  40                  45

Leu Glu Ala Asn Met Cys Leu Pro Gly Ala Ala Gly Leu Glu
    50                  55                  60

<210> SEQ ID NO 3
<211> LENGTH: 6
<212> TYPE: PRT
<213> ORGANISM: Artificial Sequence
<220> FEATURE:
<223> OTHER INFORMATION: phosphoserine consensus binding sequence
<220> FEATURE:
<221> NAME/KEY: PHOSPHORYLATION
<222> LOCATION: 4
<223> OTHER INFORMATION: The Ser residue at position 4 is phosphorylated
<220> FEATURE:
<221> NAME/KEY: VARIANT
<222> LOCATION: (1)...(6)
<223> OTHER INFORMATION: Xaa = Any Amino Acid

<400> SEQUENCE: 3

Arg Ser Xaa Ser Xaa Pro
1               5
```